United States Patent
Paliwal et al.

(10) Patent No.: US 9,486,646 B2
(45) Date of Patent: Nov. 8, 2016

(54) SYSTEM AND METHOD FOR CONTROL OF EXTERNAL BEAM RADIATION

(71) Applicant: Wisconsin Alumni Research Foundation, Madison, WI (US)

(72) Inventors: Bhudatt Paliwal, Madison, WI (US); Yue Yan, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 5 days.

(21) Appl. No.: 14/473,858

(22) Filed: Aug. 29, 2014

(65) Prior Publication Data
US 2016/0059040 A1 Mar. 3, 2016

(51) Int. Cl.
*A61N 5/10* (2006.01)

(52) U.S. Cl.
CPC .......... *A61N 5/1042* (2013.01); *A61N 5/1067* (2013.01); *A61N 2005/1095* (2013.01)

(58) Field of Classification Search
CPC .... A61N 5/1042; G21K 1/10; A61B 6/4035; A61B 6/032
USPC .................................................. 378/65, 156
See application file for complete search history.

(56) References Cited

U.S. PATENT DOCUMENTS

| | | | |
|---|---|---|---|
| 3,917,954 A | 11/1975 | Boge | |
| 3,950,651 A * | 4/1976 | Flocee | A61B 6/06 378/147 |
| 6,148,062 A | 11/2000 | Romeas | |
| 2011/0033028 A1 | 2/2011 | Parsai et al. | |

OTHER PUBLICATIONS

Chofor, et al., A Direction-Selective Flattening Filter for Clinical Photon Beams. Monte Carlo Evaluation of a New Concept, Physics in Medicine and Biology, 2011, 56:4355-4376.

* cited by examiner

*Primary Examiner* — Courtney Thomas
(74) *Attorney, Agent, or Firm* — Quarles & Brady, LLP

(57) ABSTRACT

A system for radiation therapy includes an ionizing radiation source for producing a beam oriented along an axis aligned with a target volume for delivering ionizing radiation to the target volume along a beam path and at a dose rate, wherein the beam includes a soft spectrum and a hard spectrum. The system also includes a filter arranged within the beam path and including a central aperture that is free of beam-filtering material, wherein the central aperture is surrounded by a beam-filtering material having a thickness dimension selected and positioned in the beam path to highly attenuate the soft spectrum of the beam to reduces external scatter of the beam and allow a majority of the hard spectrum of the beam to pass through the central aperture unfiltered. The beam path is free of beam-filtering material arranged to attenuate a central portion of the beam.

22 Claims, 12 Drawing Sheets

SYSTEM AND METHOD FOR CONTROL OF EXTERNAL BEAM RADIATION

CROSS-REFERENCE TO RELATED APPLICATIONS

Not applicable.

STATEMENT REGARDING FEDERALLY SPONSORED RESEARCH

Not applicable.

BACKGROUND

The disclosure relates, in general, to radiation filters and, more particularly, to radiation filters for use with external beam radiation systems.

Conventional external beam radiation therapy, also referred to as "teletherapy," is commonly administered by directing a linear accelerator ("LINAC") to produce beams of ionizing radiation that irradiates the defined target volume in a patient. The radiation beam is a single beam of radiation that is delivered to the target region from several different directions, or beam paths. Together, the determination of how much dose to deliver along each of these beam paths constitutes the so-called radiation therapy "plan." The purpose of the treatment plan is to accurately identify and localize the target volume in the patient that is to be treated.

Intensity modulated radiation therapy ("IMRT") is an external beam radiation therapy technique that utilizes computer planning software to produce a three-dimensional radiation dose map, specific to a target tumor's shape, location, and motion characteristics. Various regions within a tumor and within the patient's overall anatomy may receive varying radiation dose intensities through IMRT, which treats a patient with multiple rays of radiation, each of which may be independently controlled in intensity and energy. Each of these rays or beams is composed of a number of sub-beams or beamlets, which may vary in their individual intensity, thereby providing the overall intensity modulation. Because of the high level of precision required for IMRT methods, detailed data must be gathered about tumor locations and their motion characteristics. In doing so, the radiation dose imparted to healthy tissue can be reduced while the dose imparted to the affected region, such as a tumor, can be increased. In order to achieve this, accurate geometric precision is required during the treatment planning stage.

Image-guided radiation therapy ("IGRT") employs medical imaging, such as computed tomography ("CT"), concurrently with the delivery of radiation to a subject undergoing treatment. In general, IGRT is employed to accurately direct radiation therapy using positional information from the medical images to supplement a prescribed radiation delivery plan. The advantage of using IGRT is twofold. First, it provides a means for improved accuracy of the radiation field placement. Second, it provides a method for reducing the dose imparted to healthy tissue during treatment. Moreover, the improved accuracy in the delivery of the radiation field allows for dose escalation in the tumor, while mitigating dose levels in the surrounding healthy tissue.

In general, flattening filters (FF) have been included as a component of LINAC systems over the past decades. Moreover, flattening-filter-free (FFF) treatment beams have been studied and implemented in recent years. FFF treatment beams offer distinct advantages such as higher dose rate and rapid beam modulation in advanced radiation therapy techniques such as IMRT, stereotactic body radiation therapy (SBRT) and gated treatment (GT). In one aspect, the FFF beam may limit the scatter generated by the FF within the gantry head. The reduced scatter can potentially benefit the dose sparing effect to peripheral organs. However, the soft spectrum of the FFF beam may increase the superficial and internal scatter dose in a patient's body and potentially compromise the dose sparing effect. Accordingly there is a need for systems and methods that overcome one or more of the aforementioned problems.

SUMMARY

The present disclosure overcomes the aforementioned drawbacks by providing a system and method for filtering external beam radiation. In one aspect, the present disclosure provides a soft-spectrum-filter (SPECTER). In some embodiments, a SPECTER may be used to remove the soft part of the FFF beam. The material and dimensions of the SPECTER may be optimized to control external scatter and loss in high dose rates compared with systems employing FFF beams.

In accordance with one aspect of the present disclosure, a radiation therapy system is provided that includes an ionizing radiation source for producing a beam oriented along an axis aligned with a target volume for delivering ionizing radiation to the target volume along a beam path and at a dose rate, wherein the beam includes a soft spectrum and a hard spectrum. The system also includes a filter arranged within the beam path and including a central aperture that is free of beam-filtering material, wherein the central aperture is surrounded by a beam-filtering material having a thickness dimension selected and positioned in the beam path to highly attenuate the soft spectrum of the beam to reduces external scatter of the beam and allow a majority of the hard spectrum of the beam to pass through the central aperture unfiltered. The beam path is free of beam-filtering material arranged to attenuate a central portion of the beam.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 5A shows the fluences of the FFF beam and tin and lead SPECTER beams with circular cross sections, FIG. 5B shows the fluences of tin and lead SPECTER beams with circular and square cross sections, and FIG. 5C shows the details of FIG. 5B in the energy range of 0-0.5 MeV.

FIG. 6A shows the beam profiles of the FFF beam and the SPECTER beams, FIG. 6B shows the dose profiles in the tail region in FIG. 6A, and FIG. 6C shows the internal scatter dose for the FFF beam and the SPECTER beams.

FIG. 7A shows the beam profiles of the FFF beam and the SPECTER beams, FIG. 7B shows the dose profiles of the tail region in FIG. 7A, and FIG. 7C shows the internal scatter dose for the FFF beam and the SPECTER beams.

FIG. 8A shows the dose profiles of the FFF beam and the SPECTER beam with 25×25 cm2 and 40×40 cm2 field sizes, FIG. 8B shows the internal scatter dose of the FFF beam and the SPECTER beam with a 25×25 cm2 field size, and FIG. 8C shows the internal scatter dose of the FFF beam and the SPECTER beam with a 40×40 cm2 field size.

Like numbers will be used to describe like parts from Figure to Figure throughout the following detailed description.

DETAILED DESCRIPTION

Figure 1:
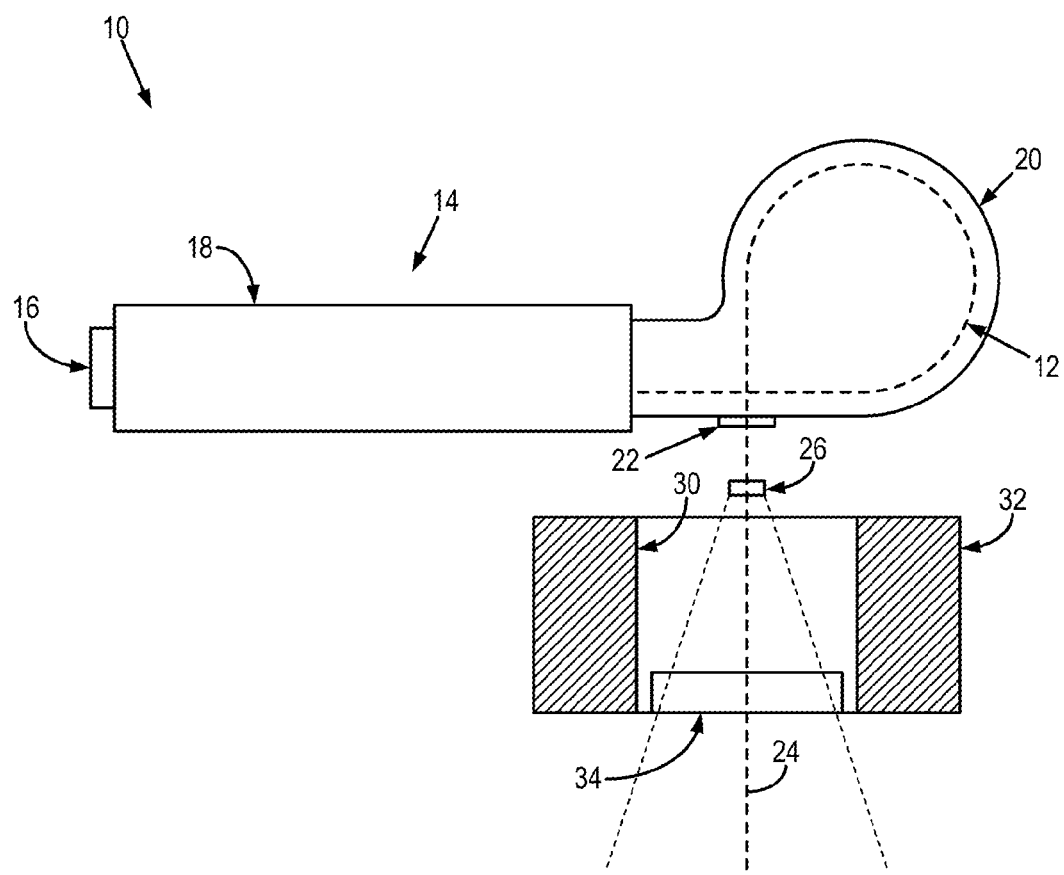
FIG. 1 is an example of a radiation treatment device in accordance with the present disclosure.

The present disclosure is presented in several varying embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment.

The described features, structures, or characteristics of the disclosure may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the disclosure.

In general, one aspect of the present disclosure includes a system and method for the control and delivery of external beam radiation. Technical advances in modern radiation therapy (RT) have led to rapid gains in treatment delivery methods. Examples include static IMRT and rotational IMRT (e.g. VMAT and helical tomotherapy (HT)) techniques. These delivery methods provide improved conformity of the dose to planning target volume (PTV) with steeper dose gradients in surrounding healthy tissues, thereby leading to better tumor control probability (TCP). However, limitations still exist. For example, as compared with 3D conformal radiation therapy (3D-CRT), IMRT tends to increase the dose to surrounding tissues in order to provide the optimal dose. This may negatively impact the normal tissue complication probability (NTCP). Another limitation may include prolonged treatment times required to deliver the dose for IMRT as compared with traditional techniques. For techniques such as SBRT which require a large number of monitor units (MUs) to deliver the dose, such limitations become more pronounced. A large number of MUs may lead to unacceptable dose deviation caused by intra-fractional motion of patients. Several investigations have shown that these limitations could lead to increased probability of cancer induction due to radiation.

One possible solution implemented in some of the modern RT delivery systems to shorten the treatment time and reduce the scatter dose is to remove the FF. This approached was introduced primarily to generate beams with flat profiles. Advancements in RT beam modulation have reduced to need for FF in modern RT systems. By comparison, it may be useful to provide FFF bremsstrahlung photon beams generated by modern LINACS for clinical applications. Compared with the flattened beam, the FFF beam has many advantages, including: increased dose rates (about 2 to about 5 times greater as compared with a flattened beam); reduced dose to OARs in some clinical applications; reduction of scatter from the gantry head and lower leakage dose (~70% reduction); reduced neutron contamination to a patient (~73% reduction) when using high-energy radiation to deliver treatments; and reduced uncertainty in dose calculation caused by scatter from the FF. These unique advantages of the FFF beam may lead to shorter treatment time (e.g., for treatments with large MUs), better dose sparing effect to OARs and lower risk for secondary cancer induced by radiation.

One of the limitations for the FFF beam is its "softer" photon beam. That is, a radiation beam can be divided into a soft spectrum and a hard spectrum. As used herein a soft spectrum refers to relatively greater low energy photons in the beam. A hard spectrum refers to relatively greater high energy photons in the beam. The hard spectrum is desirable because it represents the radiation dose that is targeted to perform the therapy. The soft spectrum is less desirable, for example, because it is prone to scatter and, thus, can undesirably irradiate healthy tissue by scattering away from the beam path or into peripheral tissue. The soft spectrum of the FFF beam may increase the internal scatter within the patient's body, which in turn may lead to higher doses to OARs and the skin in spite of a large decrease in external scatter. One possible solution to improve the dose sparing effect of the FFF beam may be to modify the spectrum of the photon beam. It will be appreciated that while various specific examples of a SPECTER are presented herein, the definition of the SPECTER is general and may be applied to other systems without an FF.

In one aspect, the SPECTER may be used to achieve unexpectedly desirable decreases the internal scatter dose caused by the soft spectrum of an FFF beam. Accordingly, a SPECTER may be incorporated into a system such as an external beam radiation system to reduce the scatter dose to OARs as compared with FFF or flattened beams. Moreover, a SPECTER may be used to maintain a relatively high dose rate as compared with FFF or flattened beams. In one aspect, a SPECTER may have a low density near the central axis (filled with air) in order to maintain a higher dose rate.

In general, the present disclosure can be implemented in an external beam radiation therapy system. Examples of external beam therapy systems include image-guided radiation therapy ("IGRT") systems; intensity-modulated radiation therapy ("IMRT") systems; intensity-modulated arc therapy ("IMAT") systems, which may include volumetric arc therapy ("VMAT") systems; tomotherapy systems; and the like.

Referring to FIG. 1, an example of a radiation treatment device 10 is illustrated. An electron beam 12 is generated in an electron accelerator 14. The electron accelerator 14 generally includes an electron gun 16, a waveguide 18, and a guide magnet 20.

The electron beam 12 is generated by the electron gun 16 under the control of a trigger system and injector, as is known in the art. The electron beam 12 is accelerated and guided by the waveguide 18. For instance, radio frequency signals are provided to the wave guide 18 and used to generate an electromagnetic field. The electrons injected by the injector and emitted by the electron gun 16 are accelerated by this electromagnetic field in the waveguide 18, and the accelerated electron beam 12 exits at the end opposite to the electron gun 16.

The electron beam 12 enters the guide magnet 20 and from there is guided through a window 22 along a beam axis 24. In some embodiments, the electron beam 12 impinges on a target 26, which results in the generation of an x-ray beam 28 oriented along the beam axis 24. The x-ray beam travels through an aperture 30 of a shield block 32 where it encounters a filter 34, which, as will be described, may advantageously be a SPECTER or SPECTER in combinations with other filter or collimation systems.

Figure 2:
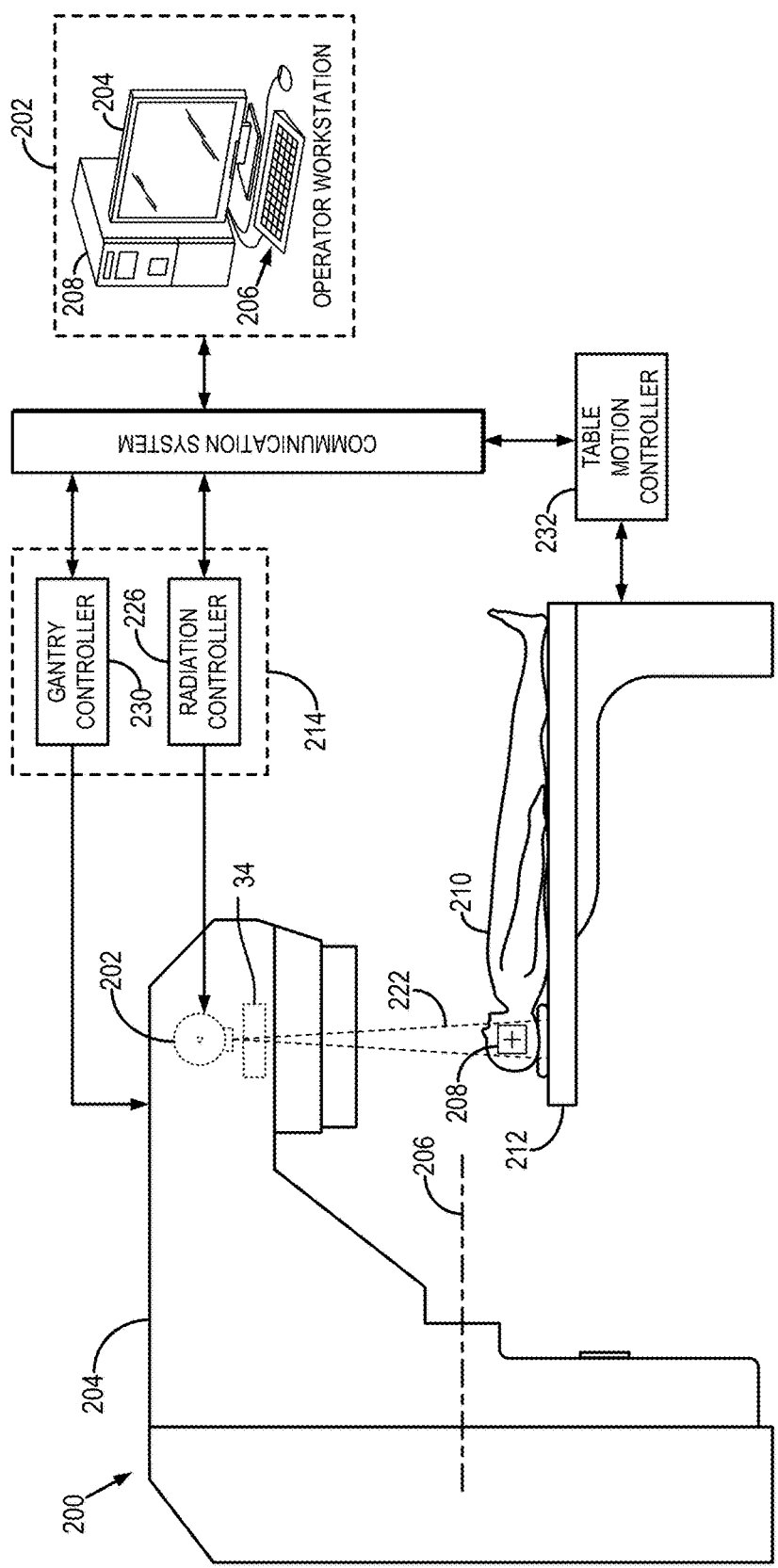
FIG. 2 is an example of an external beam radiation therapy system.

Referring to FIG. 2, an example of an external beam radiation therapy system 200 includes a radiation source 202, such as an x-ray source, that is housed at an end of a gantry 204, which in some embodiment can be configured to rotate about a rotation axis 206. The gantry 204 allows the radiation source 202 to be aligned in a desired manner with respect to a target volume 208 in a subject 210 positioned on a patient table 212. A control mechanism 214 controls the delivery of radiation from the radiation source 202 to the target volume 208, and in some embodiments may control the rotation of the gantry 204.

The external beam radiation therapy system 200 includes a computer 216 that receives commands and scanning parameters from an operator via a console 218, or from a memory or other suitable storage medium. An associated display 220 allows the operator to observe data from the computer 216, including images of the subject 210 that may be used to review or modify the treatment plan, and to position the subject 210 by way of appropriately adjusting the position of the patient table 212. The operator supplied commands and parameters may also be used by the computer 216 to provide control signals and information to the control mechanism 214.

The radiation source 202 is controlled by a radiation controller 226 that forms a part of the control mechanism 214, and which provides power and timing signals to the radiation source 202.

As mentioned above, in some embodiments the radiation source 202 is mounted on a gantry 204 that can be configured to rotate about a rotation axis 206 so that a radiation beam 222 may irradiate the target volume 208 in the subject 210 from a variety of different gantry angles, $\theta_i$. In these embodiments, a gantry controller 230, which forms a part of the control mechanism 214, provides the signals necessary to rotate the gantry 204 and, hence, to change the position of the radiation source 202 and the gantry angle, $\theta_i$, of the radiation beam 222 for the radiation therapy. The gantry controller 230 connects with the computer 216 so that the gantry 204 may be rotated under computer control, and also to provide the computer 216 with a signals indicating the gantry angle, $\theta_i$, to assist in that control.

The position of the patient table 212 may also be adjusted to change the position of the target volume 208 with respect to the radiation source 202 by way of a table motion controller 232, which is in communication with the computer 216.

Figure 3:
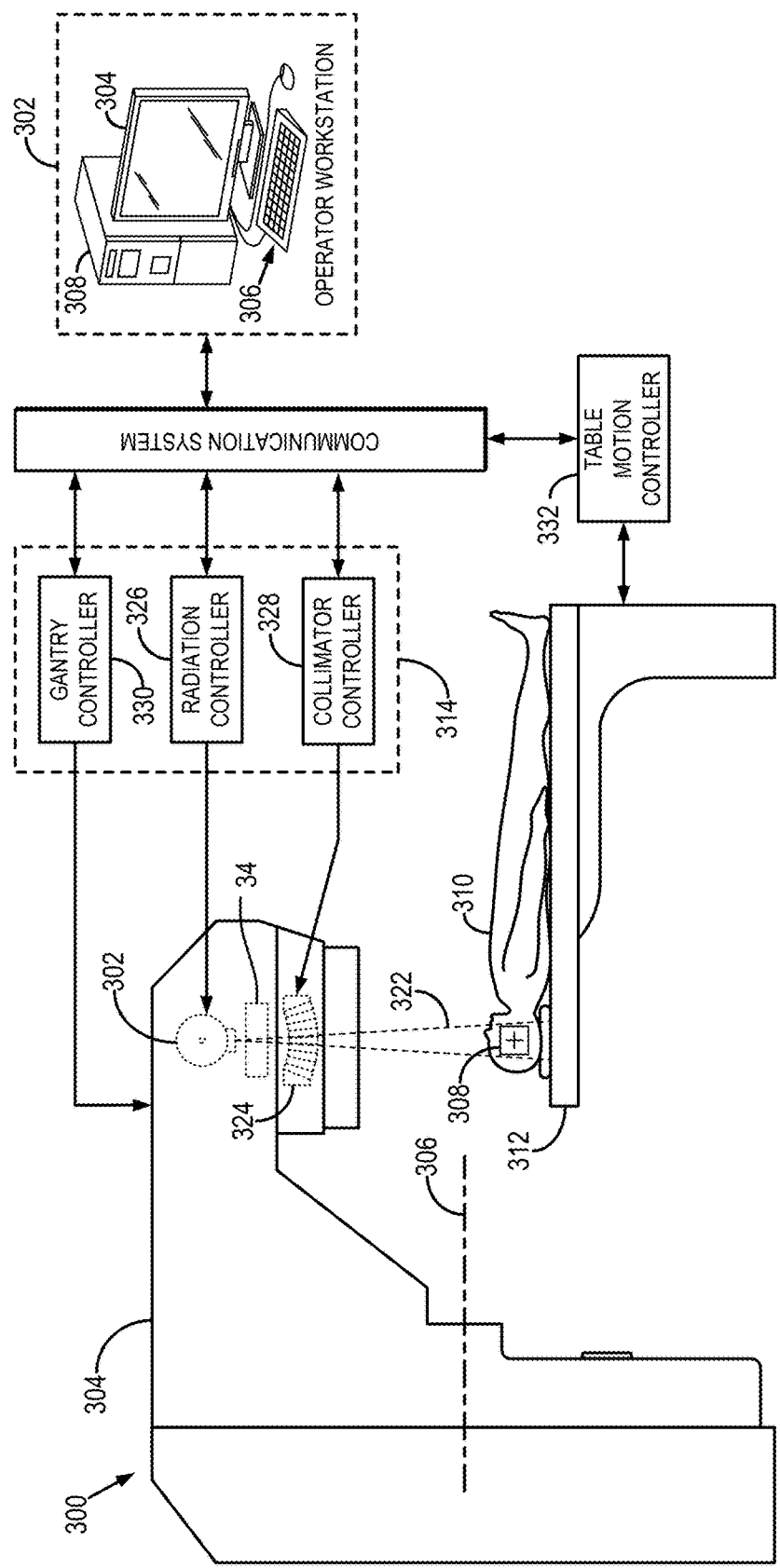
FIG. 3 is an example of an intensity-modulated arc therapy ("IMAT") system in accordance with the present disclosure.

Referring to FIG. 3, an example of an intensity-modulated arc therapy ("IMAT") system 300 includes a radiation source 302, such as an x-ray source, that is housed at an end of a rotatable gantry 304 that rotates about a rotation axis 306. The rotatable gantry 304 allows the radiation source 302 to be aligned in a desired manner with respect to a target volume 308 in a subject 310 positioned on a patient table 312. A control mechanism 314 controls the rotation of the gantry 304 and the delivery of radiation from the radiation source 302 to the target volume 308. The IMAT system 300 includes a computer 316 that receives commands and scanning parameters from an operator via a console 318, or from a memory or other suitable storage medium. An associated display 320 allows the operator to observe data from the computer 316, including images of the subject 310 that may be used to review or modify the treatment plan, and to position the subject 310 by way of appropriately adjusting the position of the patient table 312. The operator supplied commands and parameters may also be used by the computer 316 to provide control signals and information to the control mechanism 314.

The radiation source 302 produces a radiation beam 322, or "field," that is modulated by a collimator 324. The collimator 324 may include a multileaf collimator that is composed of a plurality of independently adjustable collimator leaves. In such a configuration, each leaf in the collimator 324 is composed of an appropriate material that inhibits the transmission of radiation, such as a dense radioopaque material, and may include lead, tungsten, cerium, tantalum, or related alloys.

As illustrated, the filer 34 may be arranged between the source 302 and the collimator 324. By arranging the filter 34 in this configuration, the size and material of the filter 34 may be controlled and the beam 322 is generally consistent when arriving at the filter 34 (as opposed to the variation in the beam 322 following collimation by a dynamically-variable collimator 324). However, in some configurations, the filter may be arranged closer to the subject to thereby arrange the collimator 324 between the filter 34 and the source 302.

The radiation source 302 is mounted on a rotatable gantry 304 that rotates about a rotation axis 306 so that the radiation beam 322 may irradiate the target volume 308 in the subject 310 from a variety of gantry angles, $\theta_i$. The radiation source 302 is controlled by a radiation controller 326 that forms a part of the control mechanism 314, and which provides power and timing signals to the radiation source 302.

A collimator controller 328, which forms a part of the control mechanism 314, controls the movement of each of the collimator leaves in and out of its corresponding sleeve. The collimator controller 328 moves the collimator leaves rapidly between their open and closed states to adjust the aperture shape of the collimator 324 and, therefore, the shape and fluence of the radiation beam 322. The collimator controller 328 receives instructions from the computer 316 to allow program control of the collimator 324.

A gantry controller 330, which forms a part of the control mechanism 314, provides the signals necessary to rotate the gantry 304 and, hence, to change the position of the radiation source 302 and the gantry angle, $\theta_i$, of the radiation beam 322 for the radiation therapy. The gantry controller 330 connects with the computer 316 so that the gantry 304 may be rotated under computer control, and also to provide the computer 316 with a signals indicating the gantry angle, $\theta_i$, to assist in that control. The position of the patient table 312 may also be adjusted to change the position of the target volume 308 with respect to the radiation source 302 by way of a table motion controller 332, which is in communication with the computer 316.

During operation of the IMAT system 300, the collimator controller 328 receives, from the computer 316, segmentation information indicating the aperture shape to be used for each gantry angle, $\theta_i$, during each sweep of the radiation source 302. The segmentations describe the intensity of the radiation beam 322 that is desired for each gantry angle, $\theta_i$.

As illustrated in FIGS. 2 and 3, an external beam radiation system may further include a filter 34 as detailed in FIG. 1. In some embodiments, the filter may be a SPECTER as described in greater detail herein. In some embodiments, a SPECTER may be placed inside the gantry head. In one aspect, placing a SPECTER in the gantry head may remove the unwanted external scatter generated by the SPECTER itself.

Figure 4A:
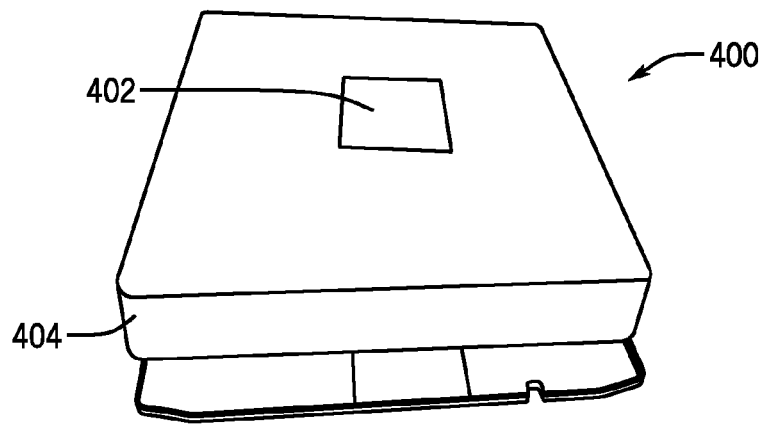
FIGS. 4A-4C show example geometries of soft-spectrum-filters (SPECTERs) in accordance with the present disclosure.
Figure 4B:
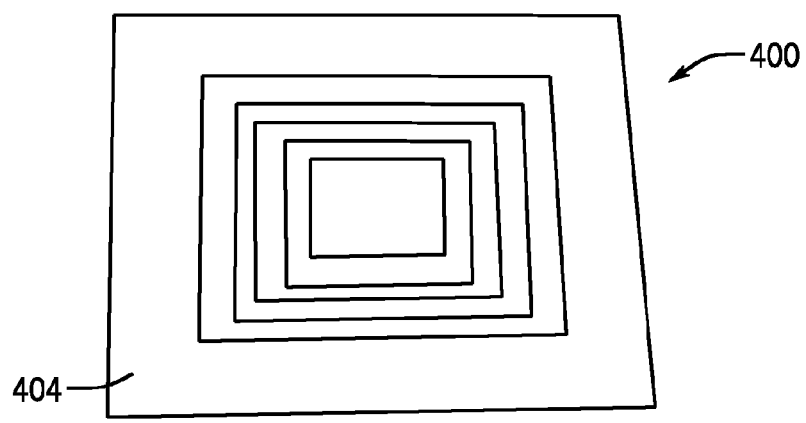
Figure 4C:
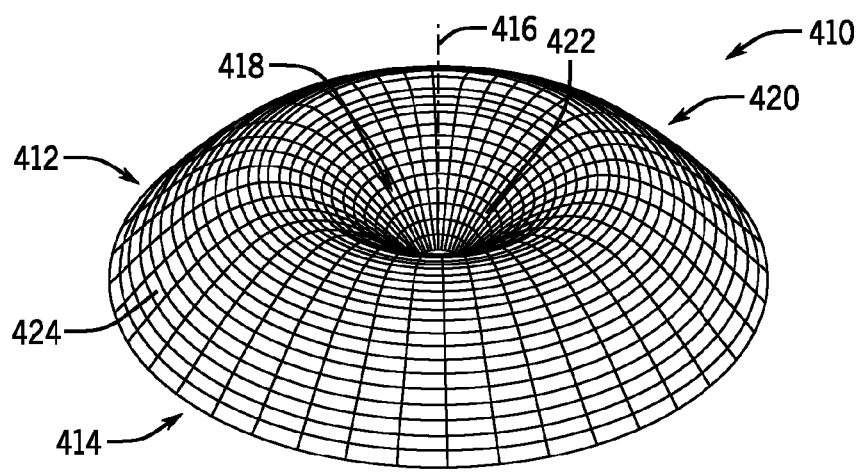

Varying geometries and materials may be used in the design of a SPECTER as illustrated in FIGS. 4A-4C. In one example, a SPECTER 400 may have a rectangular profile with a central aperture 402 and an edge 404. In one example, the edge 404 may have a thickness dimension of about 1 mm to about 10 cm. As illustrated, a series of steps 406 may be formed between the central aperture 402 and the edge 404. The steps 406 may be of different sizes or of a common size. As will be explained, the size and shape of the steps and their position relative to the size and shape of the central aperture 402 may be selected to match the geometry of the radiation beam.

Referring to FIG. 4C, a geometry is illustrated that may be particularly advantageous. As shown in FIG. 4C, a SPECTER 410 may have a circular periphery 412. The SPECTER 410 extends from a generally planar base 414 along a central axis 416 to form a concave shape about a central portion 418 that is, preferably, free of attenuating filter material. That is, the central portion 418, preferably, forms an aperture. Thus, the SPECTER 410 rises along the central axis 416 from the base 414 to a pinnacle 420 located between the central axis 416 and the periphery 412.

As will be described, the SPECTER 410 may have various geometries that are guided by the goal of providing a centrally-located aperture 418 that is surrounded by a beam-filtering material having a thickness dimension selected and positioned in the beam path to highly attenuate the soft spectrum of the beam to reduces external scatter of the beam and allow a majority of the hard spectrum of the beam to pass through the central aperture unfiltered. To this end, it was discovered that the soft spectrum increases with distance from the center of the beam path and the hard spectrum decreases with distance from the center of the beam path. Accordingly, a first taper 422 is formed between the aperture at the central portion 418 and the pinnacle 420 and a second taper 424 is formed between the pinnacle 420 and the periphery 412. As will be described, the shape, including the slope or angle, or even the existence, of the first taper 422 and the second taper 424 may differ therebetween. The thickness of the attenuating filter material forming the SPECTER 410 at any point between the central portion 418 and the periphery 412, and the slope or angle at any given point in the first taper 422 and the second taper 424, may be selected based on the amount of soft radiation delivered by the beam to that location of the SPECTER 410. That is, the thickness may be selected to control soft radiation, for example, maximizing attenuation or stopping soft radiation. On the other hand, the thickness may likewise be selected to control attenuation of hard radiation, for example, to minimize attenuation of the hard part of the spectrum. Thus, at the periphery 412, the thickness may be relatively greater than the central portion 418. For example, a peripheral region 412 may have a thickness configured to decrease the internal scatter to the peripheral regions 412 outside the treatment field. When moving further from a central axis, 416, the thickness of the SPECTER 410 may decrease relative to the peripheral region 412, for example, to correspond with the low fluence of photons in this region. However, as illustrated in FIGS. 4A and 4B, the far peripheral regions 414 may not be tapered. That is, the second taper 424 may be removed. As follows below, a variety of material and shape considerations may be balanced to select the optimum geometry for the SPECTER 410 for a given beam to be filtered.

Figure 5A:
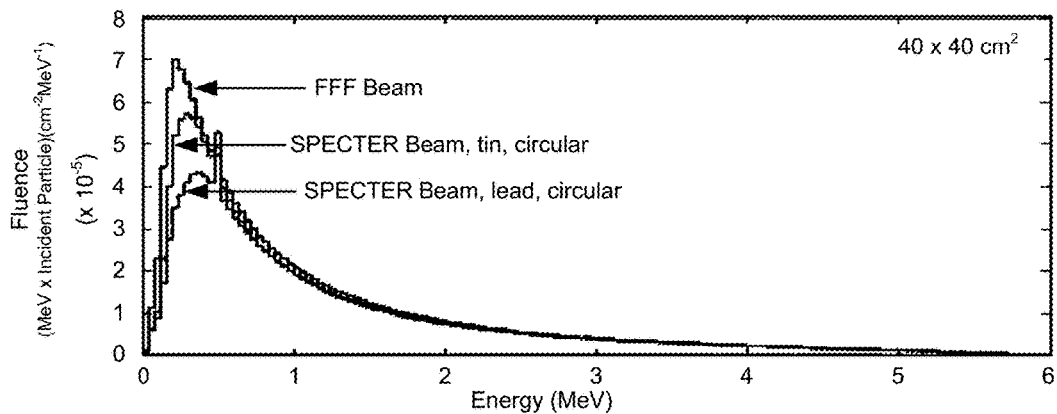
FIGS. 5A-5C are plots of fluences of FFF and the SPECTER beams for 40×40 cm$^2$ field size, where
Figure 5B:
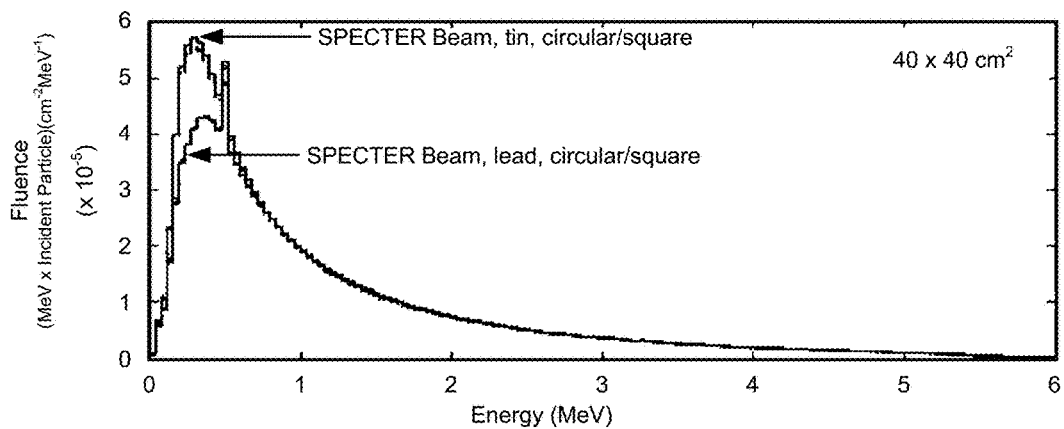
Figure 5C:
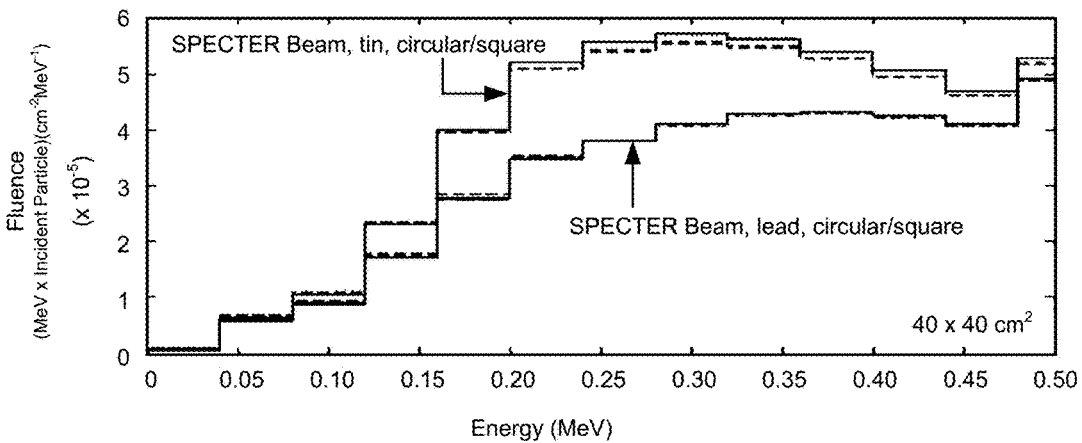

With reference to FIG. 5A-5C, lead was observed to attenuate more soft photons compared with tin and a lead SPECTER with a circular cross section provides the greatest attenuation for the soft photons as compared with the other three designs. The SPECTERs were made of lead and tin with circular and square cross sections. Total dose and internal scattered dose were calculated and the results are shown in FIGS. 6-8.

Figure 6A:
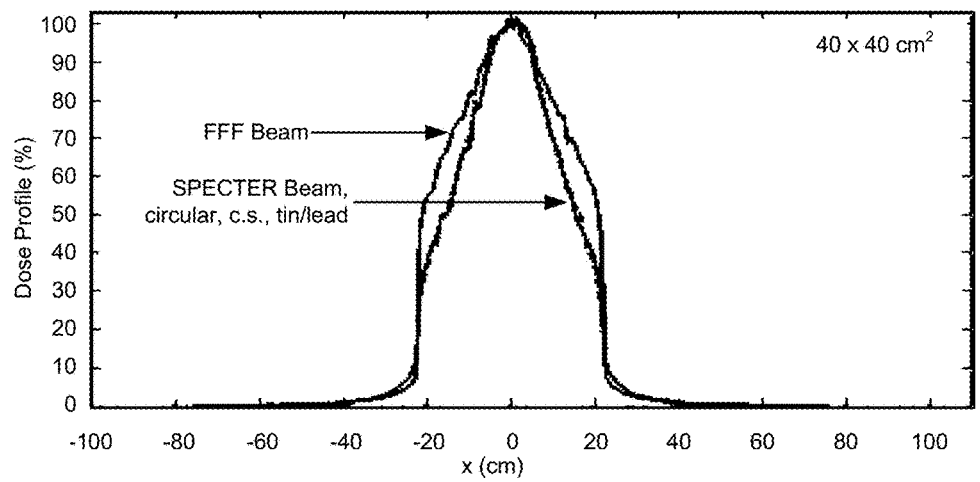
FIGS. 6A-6C are plots showing dose profiles and internal scatter dose achieved using SPECTERs beams made of lead and tin in water, where
Figure 6B:
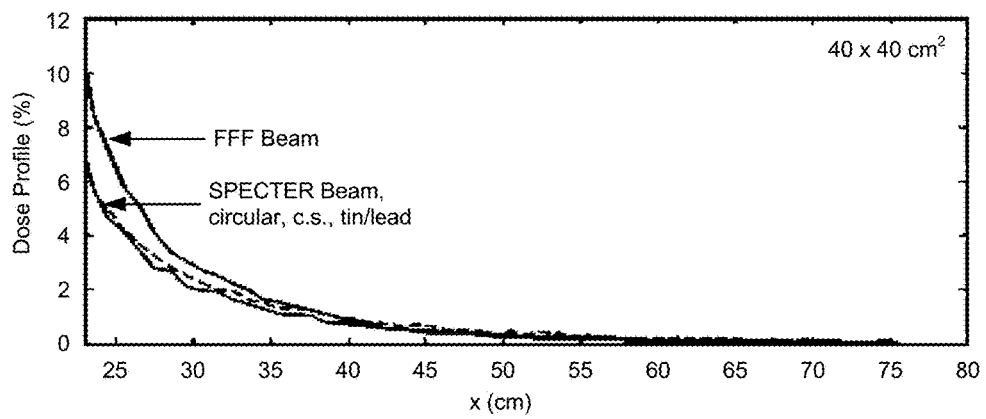
Figure 6C:
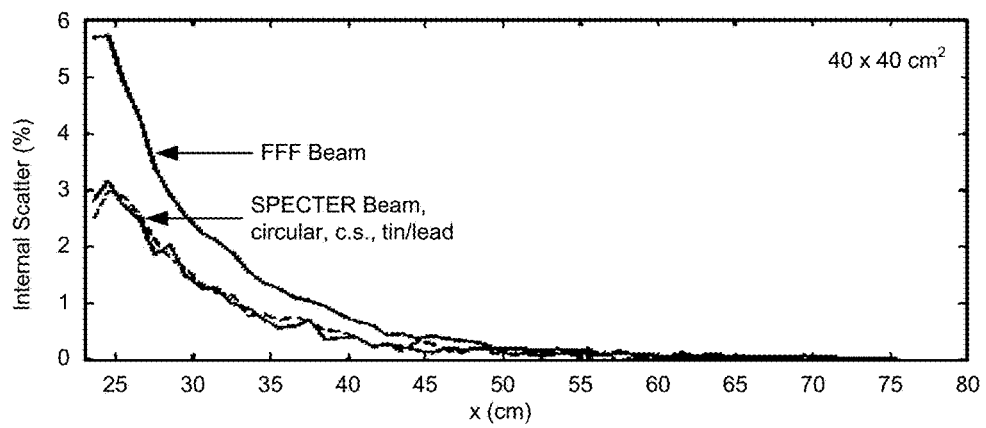

In FIGS. 6A-6C, plots are shown for SPECTERs that have circular cross sections and were made of lead (solid line) and tin (dashed line). The calculation depth was set to be at 10 cm depth with 100 cm SSD. The cutoff value for boundary between the peripheral region and the direct radiated region was chosen to be 24 cm for 40×40 cm² field size. With reference to FIGS. 6B and 6C, lead provided a better dose reduction effect a compared with tin. Lead and tin have comparative internal scatter dose reduction effect a compared with the FFF beam. In one aspect, this effect may be explained by the higher attenuation of soft photons of lead compared with tin, as shown in FIG. 5A. Even though lead tends to create more external scatter as compared with tin due to higher Z number, the higher attenuation of soft photons makes lead have lower total dose compared with tin.

Figure 7A:
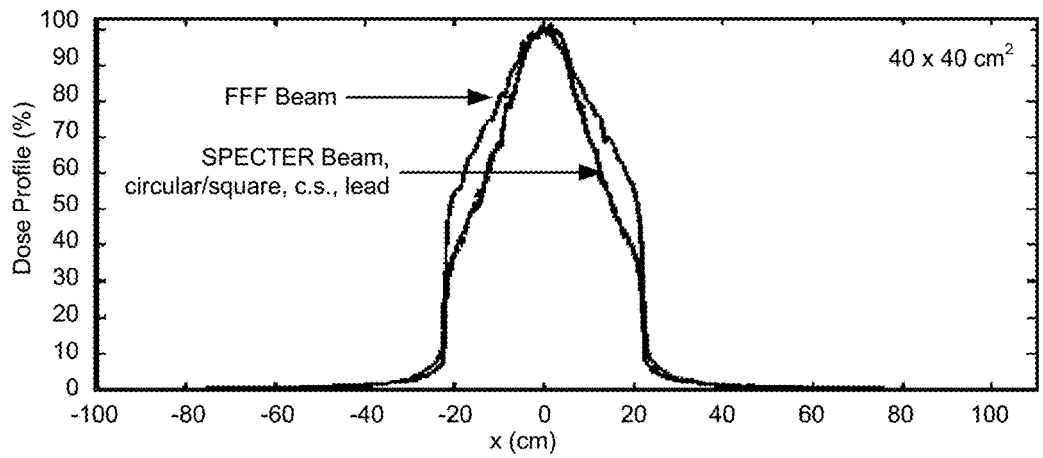
FIGS. 7A-7C are plots that show dose profiles and internal scatter dose of the lead SPECTERs with different geometries in water, where
Figure 7B:
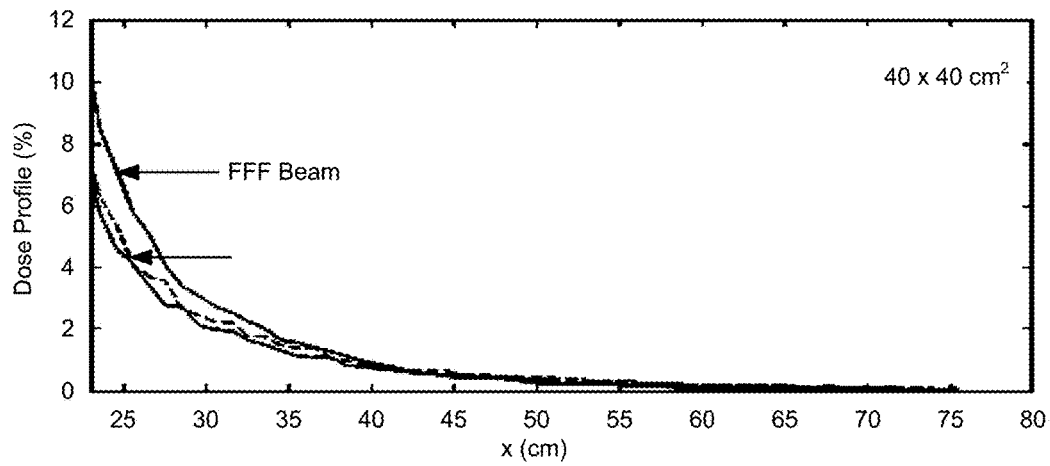
Figure 7C:
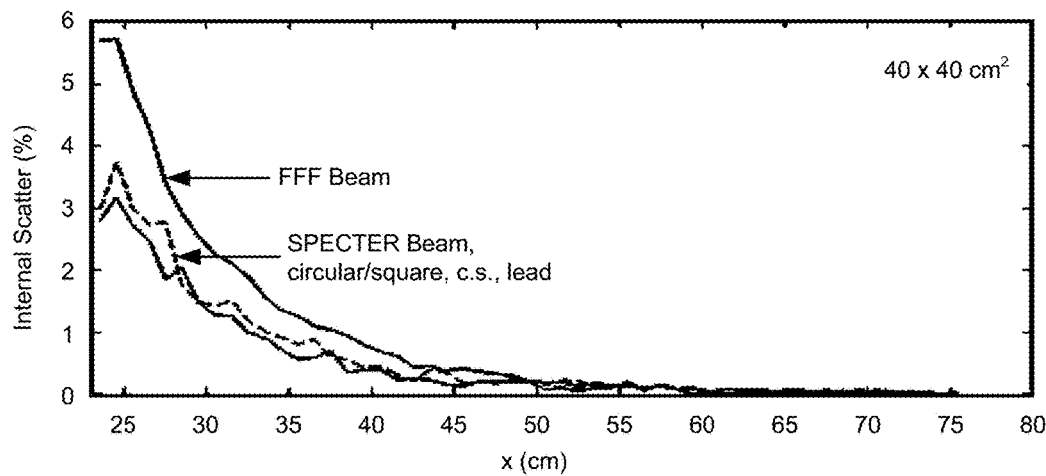

FIGS. 7a-7c show that a lead SPECTER with a circular cross-section provides a lower total dose and internal scatter dose as compared with a lead SPECTER with a square cross-section. In FIGS. 7A-7C, the SPECTERs had circular cross section (solid line) and square cross section (dashed line). The calculation depth was set to be at 10 cm depth with 100 cm SSD. The cutoff value for boundary between the peripheral region and the direct radiated region was chosen to be 24 cm for 40×40 cm² field size. In one aspect, this observation may be explained by the lower leakage of radiation of the circular cross-section as compared with the square cross-section.

Figure 8A:
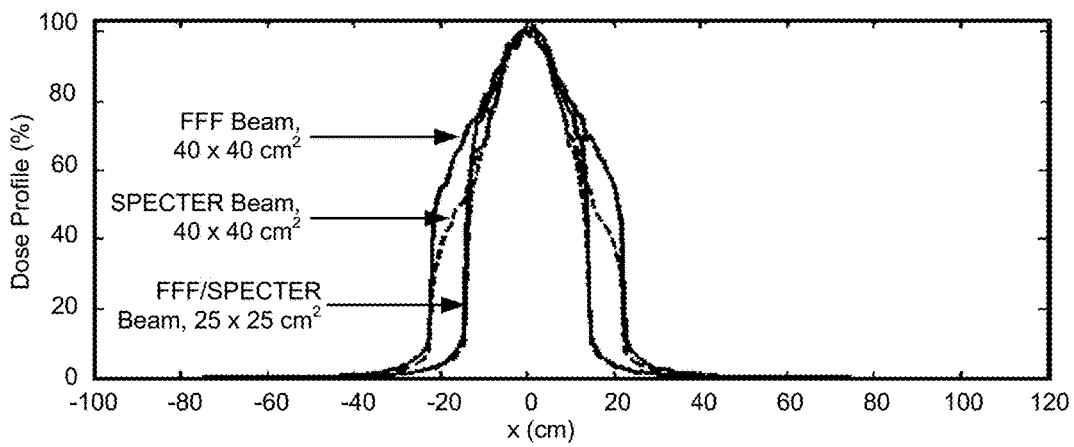
FIGS. 8A-8C are plots that show dose profiles and internal scatter dose for 6 MV photon beams in water, where
Figure 8B:
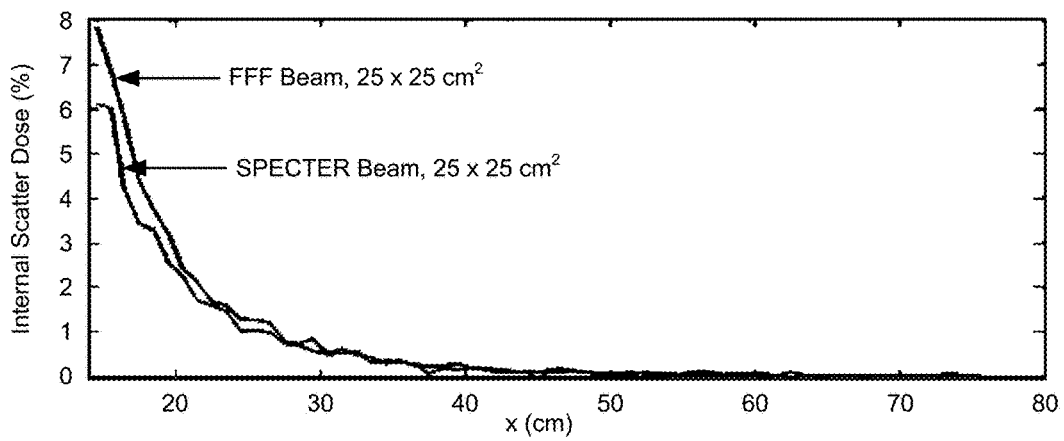
Figure 8C:
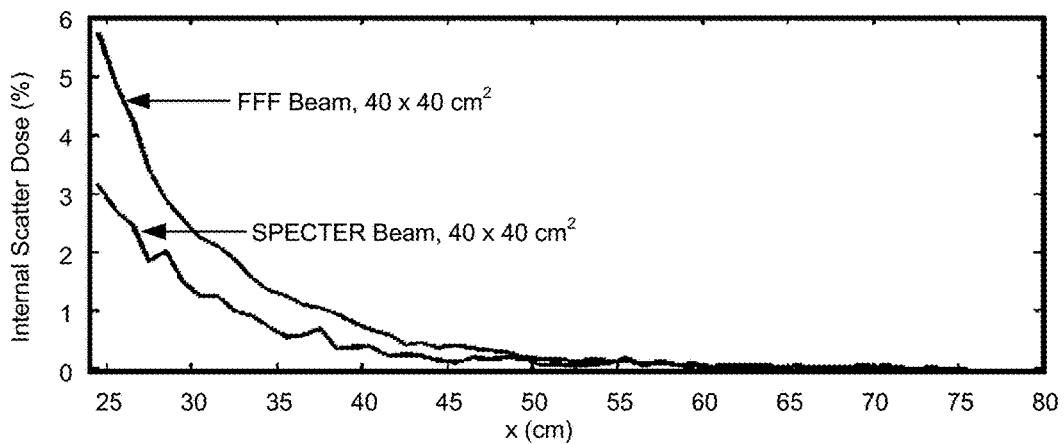
Figure 9A:
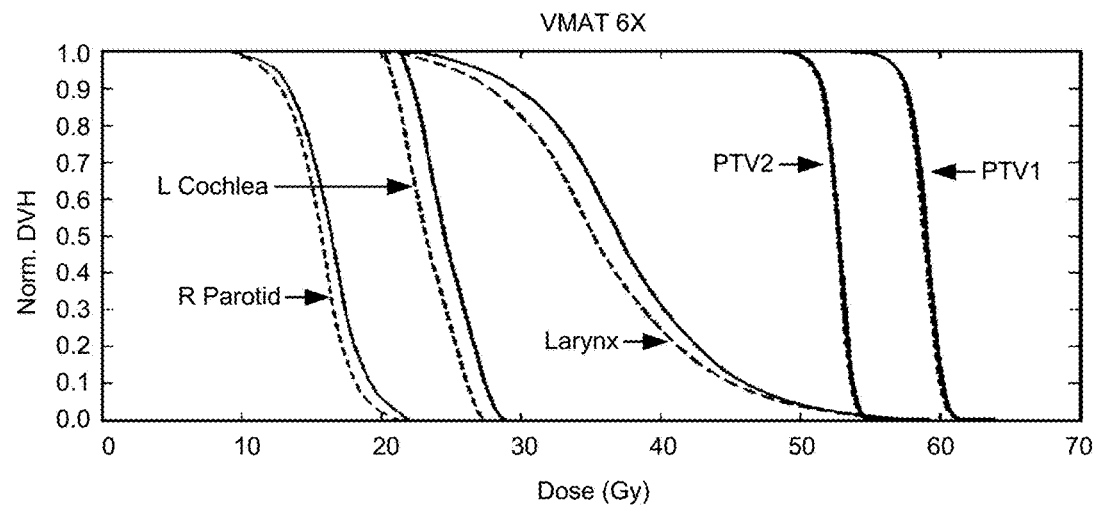
FIG. 9A is a plot that shows DVHs of head and neck cancer in case 7 for a VMAT 6 MV beam plan.
Figure 9B:
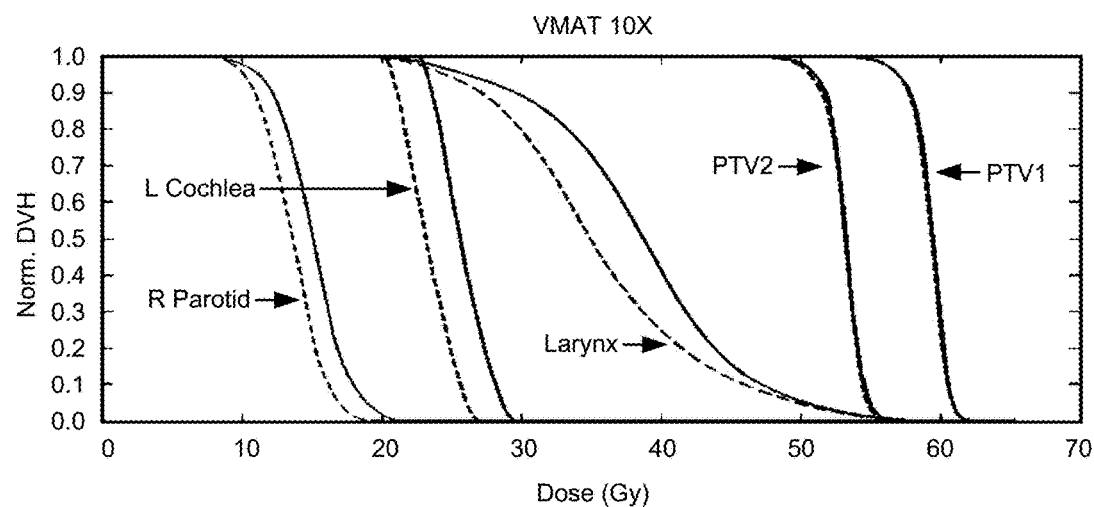
FIG. 9B is a plot that shows DVHs of head and neck cancer in case 7 for VMAT 10 MV beam plan.
Figure 10A:
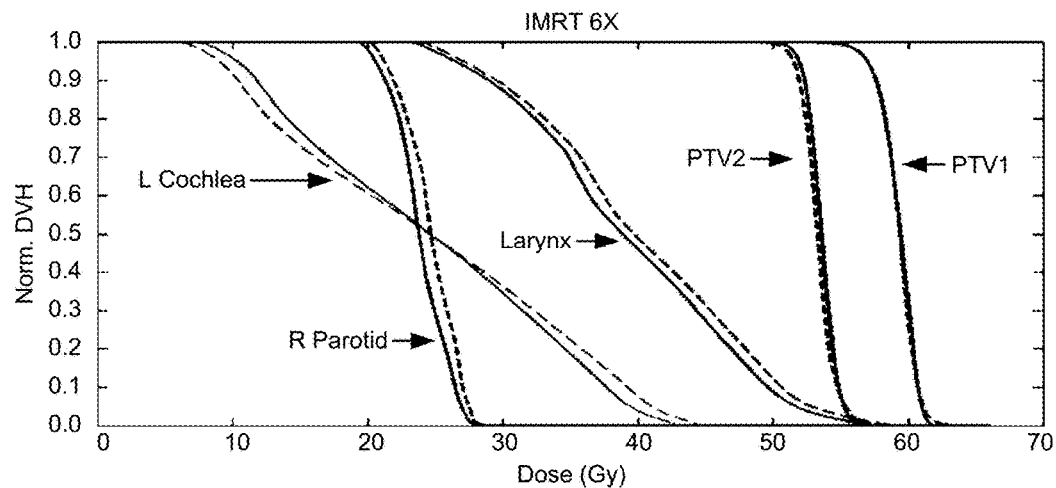
FIG. 10A is a plot that shows data for DVHs of head and neck cancer in case 7 for a static IMRT 6 MV beam plan.
Figure 10B:
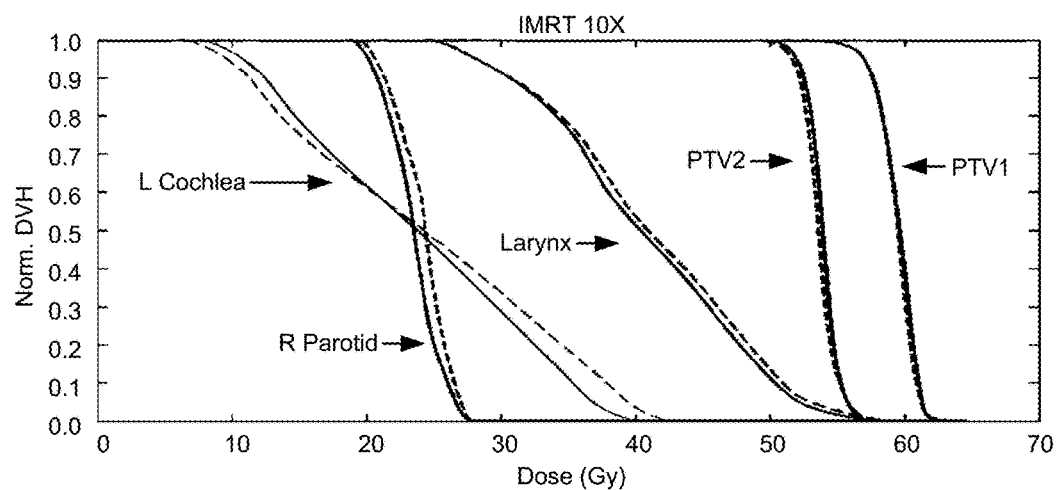
FIG. 10B is a plot that shows data for DVHs of head and neck cancer in case 7 for a static IMRT 10 MV beam plans.

FIGS. 8a-7c show that the reduction in internal scatter dose of the SPECTER beam was more pronounced for a large field size. In one aspect, a large field size may allow for more soft photons to enter the treatment field. In FIGS. 8A-8C, the calculation depth was set to be at 10 cm depth with 100 cm SSD. The cutoff value for boundary between the peripheral region and the direct radiated region was chosen to be 14 cm and 24 cm for 25×25 cm$^2$ and 40×40 cm$^2$ field sizes, respectively By removing soft photons in the FFF beam, a SPECTER may decrease the maximum dose rate for the FFF beam, as shown in FIGS. 6-8. However, a lower maximum dose rate of the FFF beam may not lead to prolonged treatment time because of the speed limitation of the MLCs for the FFF beam.

In summary, the SPECTER beam may provide a decreased total dose and internal scatter dose in the out-of-field region as compared with the FFF beam. Such a reduction effect may improve the dose sparing effect to OARs and other surrounding normal tissues. Factors that may influence the design of a SPECTER include material and geometry. Accordingly, a given material of geometry may be selected based on a given treatment approach. In one aspect, MC simulation may provide guidance in the development of a SPECTER to modify the FFF beam profile.

In one aspect, Monte Carlo (MC) simulation results have shown the advantages of the use of a SPECTER to reduce the internal scatter dose to OARs without significantly decreasing the high dose rate for the FFF beam. In some embodiments, a concave filter that provides non-uniform attenuation may be provided to obtain a desired beam profile. Moreover, different beam energies (6 MV and 10 MV) and field sizes may be tested in order to more accurately simulate clinical applications.

For a given SPECTER design, it may be useful to identify the internal dose and the external scatter dose for a given system. For the internal dose measurement, anthropomorphic phantom may be used to simulate a patient's body. TLDs may be placed inside the phantom to measure the dose in different locations. Various beam modalities may be tested, including flattened beam, FFF beam and SPECTER beam. Measurements may be benchmarked with theoretical MC calculation results to demonstrate the validity of the MC simulation. For the external scatter measurement, a large volume ion chamber may be placed in different positions to measure the scatter dose around the gantry head. The large sensitive volume of the ion chamber provides high sensitivity for external scatter dose. The external scatter dose differences may be compared among different beam modalities and beam energies.

In order to simulate the clinical application of the SPECTER beam and compare the dose differences among SPECTER, FFF and flattened beam plans, a SPECTER beam may be provided on a Varian Eclipse TPS workstation. Dose delivery techniques that may be used include static IMRT & VMAT. Photon beam energies of 6 MV and 10 MV may be selected. It has been determined that for head and neck cases with relative large treatment field sizes (~16×20 cm2), an FFF beam may show more pronounced differences as compared to a flattened beam in dose sparing effect to OARs.

EXAMPLES

Fourteen cases were selected from the Human Oncology Department at the University of Wisconsin Hospital, including: head and neck cancer (5 patients); lung cancer (4 patients); prostate cancer (4 patients) and breast cancer treated with Radiation Therapy Oncology Group (RTOG) 1005 (1 patients). All patients were anonymous and a case number was used to refer to each patient. Treatment modalities included static IMRT and VMAT. A quantitative investigation of the differences between a flattened and an FFF beam based plans was carried out. Treatment parameters such as field size, beam angle and arc number were constant between experiments. Standard clinical objectives for PTVs and OARs were used to design treatment plans. For the breast cancer case, objectives were taken from the RTOG 1005 standard treatment schedule. To provide a minimal dose to OARs, primary and boost treatments were based on static IMRT techniques. Details of treatment plannings are summarized in Table 1.

TABLE 1

| Category | Beam Modality | Delivery Technique | Dose Prescription | OARs |
|---|---|---|---|---|
| Head and Neck | 6 MV and 10 MV Flattened and FFF beams | Static IMRT VMAT | 60 Gy/30 Fx. (2 pts.) 30 Gy/15 Fx. (1 pt.) 70 Gy/28 Fx. (1 pt.) 66 Gy/33 Fx. (1 pt.) | spinal cord, brainstem, brain, larynx, pharynx, parotid |
| Lung | | | 45 Gy/30 Fx. (1 pt.) 66 Gy/33 Fx. (2 pts.) 60 Gy/30 Fx. (1 pt.) | lungs, spinal cord, heart, larynx, thyroid, esophagus |
| Prostate | | | 70 Gy/28 Fx. (3 pts.) 78 Gy/39 Fx. (1 pt.) | Rectum, bladder, hips |
| Breast | | Static IMRT | 50 Gy/25 Fx. Sequential boost 12 Gy/6 Fx. (1 pt.) | lungs, heart, thyroid, skin |

A Varian TrueBeam LINAC system was commissioned on an Eclipse workstation. Static IMRT and VMAT optimizations were performed using Anisotropic Analytical Algorithm (AAA) (Version 10.0). Photon beam energies were selected to be 6 MV and 10 MV. Flattened and FFF beams were used to design the plans. For the TrueBeam system, removing the FF increased the maximum dose rate from 600 MU/min to 1400 MU/min (2400 MU/min) for 6 MV (10 MV) photon beam. For VMAT plans, a maximum dose rate was chosen to design the plans for the FFF beam. For static IMRT plans, the dose rate was about 70% of the maximum dose rate for the FFF beam due to speed limitation of the MLCs.

With the exception of the breast cancer case, eight treatment plans were designed for each study case. DICOM files were exported from Eclipse. The image and dose files were further imported into a Matlab® (MathWorks Inc., Matick, Mass.) based toolkit software—Computational Environment for Radiotherapy Research (CERR)—developed at Washington University. All data were calculated based on DVHs from CERR (for head and neck, lung and prostate cancer) or Eclipse work station (for breast cancer).

To investigate and compare the FFF beam with the flattened beam, the target coverage and dose to OARs was studied and compared across all plans. Ninety-five percent of the target volume was normalized to the 95% dose line for all cases to exclude the lower-mean-dose-effect to the target of the FFF beam as compared with the flattened beam. To evaluate the target coverage efficiency, four indices were analyzed, including conformity index (CI), target coverage (TC), conformity number (CN) and gradient index (GI). Indices were defined as follows:

$$CI = \frac{V_{95}}{Vt_{95}};$$

$$TC = \frac{Vt_{95}}{Vt};$$

$$CN = \frac{CI}{TC};$$

$$GI = \frac{V_{95}}{Vt_{95}}$$

Vx (Vtx) was defined as the total volume (target volume), which received at least x % of the dose prescription. TC was set equal to 95% due to the normalization of all plans. CI,N and GI were always greater than one. Indices closer to one are indicative of better target coverage and dose uniformity. Statistical tests of differences between indices of the FFF and the flattened beam plans were applied using paired sample t-test. Differences were considered to be important for P-value≤0.05.

To evaluate the biological effectiveness of different beam modalities, the biological doses were calculated, such as biological effective dose (BED) and equivalent uniform dose (EUD) based on the physical dose for both target and OARs. Gay and Niemierko's model (Equations 1-3) were applied to calculate the TCP and NTCP for targets and OARs respectively. Parameters needed to calculate the biological effectiveness were obtained from published references.

$$EUD = \left(\sum_{i=1} v_i D_i^a\right)^{\frac{1}{a}} \quad \text{(Eq. 1)}$$

$$NTCP = \frac{1}{1 + \left(\frac{TD_{50}}{EUD}\right)^{4\gamma_{50}}} \quad \text{(Eq. 2)}$$

$$TCP = \frac{1}{1 + \left(\frac{TCD_{50}}{EUD}\right)^{4\gamma_{50}}} \quad \text{(Eq. 3)}$$

Dose analyses for target coverage of four cancer sites are summarized in Tables 2-5. All parameters are average values for all patients in each category. It was observed that the FFF beam provided comparative target coverage as compared with the flattened beam.

TABLE 2

| Parameters | 6 MV | | | 10 MV | | |
|---|---|---|---|---|---|---|
| | Flattened | FFF | p | Flattened | FFF | P |
| VMAT | | | | | | |
| Relative Mean dose | 1.01 ± 0.03 | 1.01 ± 0.03 | 0.81 | 1.01 ± 0.03 | 1.01 ± 0.03 | 0.81 |
| CI | 1.21 ± 0.15 | 1.24 ± 0.18 | 0.15 | 1.51 ± 0.54 | 1.46 ± 0.45 | 0.39 |
| CN | 1.27 ± 0.16 | 1.31 ± 0.20 | 0.15 | 1.59 ± 0.57 | 1.54 ± 0.47 | 0.39 |
| GI | 10.99 ± 10.85 | 10.08 ± 9.55 | 0.20 | 8.97 ± 8.63 | 8.58 ± 8.05 | 0.24 |
| TCP | 0.85 ± 0.14 | 0.85 ± 0.14 | 0.81 | 0.85 ± 0.14 | 0.85 ± 0.14 | 0.75 |
| BED ratio(FFF/FF) | 1.00 ± 0.00 | | N/A | 1.00 ± 0.00 | | N/A |
| IMRT | | | | | | |
| Relative Mean dose | 1.00 ± 0.02 | 1.01 ± 0.03 | 0.10 | 1.00 ± 0.02 | 1.01 ± 0.03 | 0.09 |
| CI | 1.25 ± 0.14 | 1.29 ± 0.16 | 0.16 | 1.19 ± 0.09 | 1.22 ± 0.10 | 0.11 |
| CN | 1.32 ± 0.15 | 1.36 ± 0.17 | 0.16 | 1.26 ± 0.10 | 1.29 ± 0.11 | 0.11 |
| GI | 11.04 ± 11.03 | 10.80 ± 10.90 | 0.13 | 11.66 ± 12.29 | 11.18 ± 11.37 | 0.31 |
| TCP | 0.84 ± 0.15 | 0.85 ± 0.14 | 0.13 | 0.84 ± 0.14 | 0.85 ± 0.14 | 0.15 |
| BED ratio(FFF/FF) | 0.99 ± 0.01 | | N/A | 0.99 ± 0.01 | | N/A |

TABLE 3

| Parameters | 6 MV | | | 10 MV | | |
|---|---|---|---|---|---|---|
| | Flattened | FFF | p | Flattened | FFF | p |
| VMAT | | | | | | |
| Relative Mean dose | 1.01 ± 0.01 | 1.01 ± 0.01 | 0.58 | 1.01 ± 0.02 | 1.03 ± 0.03 | 0.11 |
| CI | 1.09 ± 0.06 | 1.08 ± 0.05 | 0.62 | 1.09 ± 0.07 | 1.11 ± 0.06 | 0.15 |
| CN | 1.14 ± 0.06 | 1.14 ± 0.05 | 0.62 | 1.15 ± 0.07 | 1.17 ± 0.06 | 0.15 |
| GI | 3.33 ± 0.19 | 3.31 ± 0.17 | 0.18 | 3.18 ± 0.23 | 3.12 ± 0.20 | 0.04 |
| TCP | 0.71 ± 0.06 | 0.71 ± 0.07 | 0.97 | 0.71 ± 0.07 | 0.72 ± 0.07 | 0.03 |
| BED ratio(FFF/FF) | 1.00 ± 0.01 | | N/A | 0.97 ± 0.02 | | |

TABLE 3-continued

| | 6 MV | | | 10 MV | | |
|---|---|---|---|---|---|---|
| Parameters | Flattened | FFF | p | Flattened | FFF | p |
| | | IMRT | | | | |
| Relative Mean dose | 1.01 ± 0.01 | 1.01 ± 0.01 | 0.67 | 1.01 ± 0.02 | 1.02 ± 0.01 | 0.27 |
| CI | 1.18 ± 0.02 | 1.18 ± 0.02 | 0.41 | 1.16 ± 0.02 | 1.17 ± 0.03 | 0.57 |
| CN | 1.23 ± 0.02 | 1.24 ± 0.02 | 0.41 | 1.22 ± 0.02 | 1.23 ± 0.03 | 0.57 |
| GI | 3.46 ± 0.31 | 3.50 ± 0.37 | 0.41 | 3.32 ± 0.29 | 3.36 ± 0.32 | 0.15 |
| TCP | 0.71 ± 0.06 | 0.71 ± 0.06 | 0.03 | 0.71 ± 0.06 | 0.71 ± 0.06 | 0.73 |
| BED ratio(FFF/FF) | 1.00 ± 0.01 | | N/A | 1.00 ± 0.00 | | N/A |

TABLE 4

| | 6 MV | | | 10 MV | | |
|---|---|---|---|---|---|---|
| Parameters | Flattened | FFF | p | Flattened | FFF | p |
| | | VMAT | | | | |
| Relative Mean dose | 0.99 ± 0.02 | 0.99 ± 0.02 | 0.70 | 0.99 ± 0.02 | 0.99 ± 0.02 | 0.99 |
| CI | 1.11 ± 0.03 | 1.11 ± 0.03 | 0.17 | 1.11 ± 0.03 | 1.11 ± 0.04 | 0.48 |
| CN | 1.16 ± 0.03 | 1.17 ± 0.03 | 0.18 | 1.17 ± 0.03 | 1.17 ± 0.04 | 0.48 |
| GI | 9.19 ± 9.58 | 9.08 ± 9.51 | 0.11 | 8.66 ± 8.79 | 8.73 ± 9.04 | 0.63 |
| TCP | 0.94 ± 0.07 | 0.94 ± 0.07 | 0.62 | 0.94 ± 0.07 | 0.94 ± 0.07 | 0.55 |
| BED ratio(FFF/FF) | 1.00 ± 0.00 | | N/A | 1.00 ± 0.00 | | |
| | | IMRT | | | | |
| Relative Mean dose | 0.99 ± 0.01 | 0.99 ± 0.01 | 0.90 | 0.99 ± 0.01 | 0.99 ± 0.01 | 0.18 |
| CI | 1.21 ± 0.11 | 1.21 ± 0.12 | 0.46 | 1.19 ± 0.13 | 1.18 ± 0.10 | 0.38 |
| CN | 1.27 ± 0.12 | 1.28 ± 0.13 | 0.46 | 1.26 ± 0.14 | 1.24 ± 0.11 | 0.38 |
| GI | 11.62 ± 12.41 | 11.92 ± 12.35 | 0.01 | 9.50 ± 9.48 | 10.16 ± 10.47 | 0.28 |
| TCP | 0.94 ± 0.06 | 0.94 ± 0.06 | 0.85 | 0.94 ± 0.06 | 0.94 ± 0.06 | 0.83 |
| BED ratio(FFF/FF) | 1.00 ± 0.00 | | N/A | 1.00 ± 0.00 | | N/A |

TABLE 5

| | IMRT | | | |
|---|---|---|---|---|
| | 6 MV | | 10 MV | |
| Parameters | Flattened | FFF | Flattened | FFF |
| Relative Mean dose | 1.05 | 1.05 | 1.05 | 1.05 |
| CI | 1.27 | 1.27 | 1.28 | 1.30 |
| CN | 1.35 | 1.35 | 1.35 | 1.37 |
| GI | 1.88 | 1.85 | 1.88 | 1.85 |
| TCP | 0.98 | 0.98 | 0.99 | 0.99 |
| BED ratio(FFF/FF) | 1.00 | | 1.00 | |

Doses to OARs are summarized in Tables 6-9. All ratios were calculated as the FFF beam plan over the flattened beam plan. It was observed, in general, that the FFF beam provided a lower mean dose to OARs. For maximum dose, the FFF beam plan may provide a higher dose compared with the flattened beam plan, which may compromise the final NTCP value for healthy tissues.

TABLE 6

| | 6 MV | | | | 10 MV | | | |
|---|---|---|---|---|---|---|---|---|
| Organs' name | Mean dose ratio | Max dose ratio | Mean BED ratio | NTCP ratio | Mean dose ratio | Max dose ratio | Mean BED ratio | NTCP ratio |
| | | | | VMAT | | | | |
| Lens L | 0.79 ± 0.07 | 0.84 ± 0.05 | 0.78 ± 0.08 | 0.40 ± 0.14 | 0.73 ± 0.07 | 0.77 ± 0.03 | 0.72 ± 0.08 | 0.30 ± 0.11 |
| Lens R | 0.90 ± 0.00 | 0.93 ± 0.00 | 0.90 ± 0.00 | 0.67 ± 0.00 | 0.88 ± 0.00 | 0.92 ± 0.00 | 0.88 ± 0.00 | 0.61 ± 0.00 |
| Left Cochlea | 0.97 ± 0.04 | 0.98 ± 0.04 | 0.97 ± 0.05 | 0.71 ± 0.48 | 0.94 ± 0.06 | 0.95 ± 0.06 | 0.93 ± 0.07 | 0.43 ± 0.40 |
| Right Cochlea | 0.97 ± 0.00 | 0.93 ± 0.00 | 0.96 ± 0.00 | 0.51 ± 0.00 | 0.71 ± 0.00 | 0.77 ± 0.00 | 0.70 ± 0.00 | 0.004 ± 0.00 |
| Brain | 0.95 ± 0.01 | 0.98 ± 0.01 | 0.95 ± 0.00 | 0.89 ± 0.31 | 0.93 ± 0.01 | 0.98 ± 0.00 | 0.92 ± 0.00 | 0.80 ± 0.33 |
| Larynx | 0.98 ± 0.02 | 0.99 ± 0.02 | 0.97 ± 0.02 | 0.84 ± 0.20 | 0.97 ± 0.04 | 1.00 ± 0.01 | 0.97 ± 0.05 | 0.87 ± 0.19 |
| Oral Cavity | 0.93 ± 0.08 | 0.97 ± 0.06 | 0.93 ± 0.08 | 0.79 ± 0.50 | 0.92 ± 0.08 | 0.98 ± 0.03 | 0.92 ± 0.08 | 0.73 ± 0.33 |
| Pharynx | 0.99 ± 0.00 | 1.02 ± 0.00 | 0.98 ± 0.00 | 0.87 ± 0.00 | 0.97 ± 0.00 | 1.00 ± 0.00 | 0.97 ± 0.00 | 0.78 ± 0.00 |
| Esophagus | 1.00 ± 0.03 | 0.99 ± 0.02 | 1.00 ± 0.04 | 0.91 ± 0.39 | 1.00 ± 0.05 | 0.99 ± 0.03 | 1.00 ± 0.06 | 0.97 ± 0.56 |
| Cord | 0.97 ± 0.02 | 1.00 ± 0.02 | 0.97 ± 0.02 | 0.79 ± 0.21 | 0.97 ± 0.03 | 1.00 ± 0.04 | 0.97 ± 0.04 | 0.93 ± 0.48 |
| BODY | 0.97 ± 0.01 | 1.00 ± 0.01 | 0.97 ± 0.01 | 0.97 ± 0.03 | 0.96 ± 0.01 | 1.00 ± 0.01 | 0.96 ± 0.01 | 0.99 ± 0.07 |

TABLE 6-continued

| | 6 MV | | | | 10 MV | | | |
|---|---|---|---|---|---|---|---|---|
| Organs' name | Mean dose ratio | Max dose ratio | Mean BED ratio | NTCP ratio | Mean dose ratio | Max dose ratio | Mean BED ratio | NTCP ratio |
| Brainstem | 0.91 ± 0.06 | 0.95 ± 0.08 | 0.91 ± 0.06 | 0.68 ± 0.45 | 0.88 ± 0.08 | 0.93 ± 0.11 | 0.87 ± 0.08 | 0.52 ± 0.37 |
| Eye_L | 0.82 ± 0.02 | 0.91 ± 0.05 | 0.81 ± 0.02 | 0.17 ± 0.14 | 0.79 ± 0.04 | 0.91 ± 0.00 | 0.78 ± 0.04 | 0.11 ± 0.06 |
| Eye_R | 0.86 ± 0.05 | 0.90 ± 0.05 | 0.86 ± 0.06 | 0.16 ± 0.11 | 0.84 ± 0.06 | 0.93 ± 0.01 | 0.84 ± 0.06 | 0.17 ± 0.01 |
| Lips | 0.97 ± 0.00 | 0.98 ± 0.00 | 0.97 ± 0.00 | 0.71 ± 0.00 | 0.94 ± 0.00 | 0.94 ± 0.00 | 0.93 ± 0.00 | 0.39 ± 0.00 |
| Inner Ear | 0.99 ± 0.00 | 0.99 ± 0.00 | 0.99 ± 0.00 | 0.88 ± 0.00 | 0.98 ± 0.00 | 1.00 ± 0.00 | 0.97 ± 0.00 | 0.96 ± 0.00 |
| R Parotid | 0.94 ± 0.03 | 0.96 ± 0.02 | 0.93 ± 0.03 | 0.31 ± 0.20 | 0.91 ± 0.04 | 0.96 ± 0.05 | 0.91 ± 0.04 | 0.24 ± 0.27 |
| L parotid | 0.95 ± 0.04 | 1.00 ± 0.00 | 0.96 ± 0.04 | 0.36 ± 0.33 | 0.96 ± 0.04 | 1.00 ± 0.02 | 0.96 ± 0.03 | 0.40 ± 0.45 |
| R Submandibular | 0.97 ± 0.02 | 0.98 ± 0.00 | 0.96 ± 0.02 | 0.64 ± 0.03 | 0.92 ± 0.04 | 0.96 ± 0.04 | 0.91 ± 0.04 | 0.28 ± 0.14 |
| Shoulder | 0.95 ± 0.01 | 0.98 ± 0.12 | 0.95 ± 0.01 | 1.05 ± 1.07 | 0.96 ± 0.01 | 0.98 ± 0.14 | 0.96 ± 0.01 | 1.51 ± 1.57 |
| Mandible | 0.97 ± 0.00 | 1.00 ± 0.00 | 0.97 ± 0.00 | 0.86 ± 0.00 | 0.98 ± 0.00 | 1.01 ± 0.00 | 0.97 ± 0.00 | 0.89 ± 0.00 |
| Lens L | 0.73 ± 0.02 | 0.78 ± 0.07 | 0.73 ± 0.02 | 0.29 ± 0.03 | 0.65 ± 0.03 | 0.68 ± 0.05 | 0.64 ± 0.03 | 0.17 ± 0.03 |
| Lens R | 0.85 ± 0.00 | 0.87 ± 0.00 | 0.84 ± 0.00 | 0.51 ± 0.00 | 0.69 ± 0.00 | 0.70 ± 0.00 | 0.69 ± 0.00 | 0.23 ± 0.00 |
| Left Cochlea | 0.98 ± 0.03 | 1.00 ± 0.07 | 0.98 ± 0.04 | 1.32 ± 1.29 | 1.00 ± 0.03 | 1.02 ± 0.08 | 1.00 ± 0.05 | 2.18 ± 2.25 |
| Right Cochlea | 0.91 ± 0.00 | 0.92 ± 0.00 | 0.91 ± 0.00 | 0.22 ± 0.00 | 0.83 ± 0.00 | 0.87 ± 0.00 | 0.83 ± 0.00 | 0.07 ± 0.00 |
| Brain | 0.96 ± 0.02 | 1.02 ± 0.01 | 0.97 ± 0.01 | 1.31 ± 0.33 | 0.98 ± 0.03 | 1.02 ± 0.03 | 0.99 ± 0.02 | 1.29 ± 0.12 |
| Larynx | 1.02 ± 0.02 | 1.02 ± 0.01 | 1.03 ± 0.02 | 1.57 ± 0.39 | 1.02 ± 0.01 | 1.02 ± 0.01 | 1.02 ± 0.01 | 1.42 ± 0.25 |
| Oral Cavity | 1.01 ± 0.01 | 1.02 ± 0.02 | 1.01 ± 0.01 | 1.71 ± 0.76 | 1.00 ± 0.02 | 1.01 ± 0.01 | 1.01 ± 0.02 | 1.43 ± 0.74 |
| Pharynx | 1.04 ± 0.00 | 1.03 ± 0.00 | 1.04 ± 0.00 | 1.51 ± 0.00 | 1.05 ± 0.00 | 1.01 ± 0.00 | 1.06 ± 0.00 | 1.14 ± 0.00 |
| Esophagus | 0.99 ± 0.02 | 1.01 ± 0.01 | 1.01 ± 0.02 | 1.06 ± 0.11 | 1.00 ± 0.00 | 1.01 ± 0.02 | 1.00 ± 0.00 | 1.25 ± 0.46 |
| Cord | 1.00 ± 0.01 | 1.01 ± 0.02 | 1.01 ± 0.01 | 1.26 ± 0.24 | 1.01 ± 0.00 | 1.02 ± 0.01 | 1.01 ± 0.00 | 1.32 ± 0.17 |
| BODY | 0.99 ± 0.00 | 1.01 ± 0.01 | 0.99 ± 0.00 | 1.09 ± 0.17 | 0.99 ± 0.01 | 1.04 ± 0.03 | 0.99 ± 0.01 | 1.06 ± 0.15 |
| Brainstem | 0.97 ± 0.07 | 1.00 ± 0.08 | 0.98 ± 0.08 | 2.05 ± 2.22 | 0.95 ± 0.06 | 0.97 ± 0.09 | 0.96 ± 0.06 | 1.30 ± 0.84 |
| Eye_L | 0.72 ± 0.04 | 0.81 ± 0.02 | 0.71 ± 0.04 | 0.01 ± 0.01 | 0.67 ± 0.05 | 0.73 ± 0.11 | 0.66 ± 0.05 | 0.01 ± 0.01 |
| Eye_R | 0.84 ± 0.05 | 0.93 ± 0.10 | 0.84 ± 0.05 | 0.39 ± 0.52 | 0.80 ± 0.11 | 0.85 ± 0.22 | 0.79 ± 0.11 | 0.42 ± 0.59 |
| Lips | 1.00 ± 0.00 | 1.01 ± 0.00 | 1.00 ± 0.00 | 1.35 ± 0.00 | 1.00 ± 0.00 | 0.99 ± 0.00 | 0.99 ± 0.00 | 0.75 ± 0.00 |
| Inner Ear | 0.97 ± 0.00 | 0.98 ± 0.00 | 0.97 ± 0.00 | 0.71 ± 0.00 | 0.99 ± 0.00 | 0.98 ± 0.00 | 0.99 ± 0.00 | 0.79 ± 0.00 |
| R Parotid | 1.00 ± 0.02 | 1.01 ± 0.01 | 1.00 ± 0.02 | 0.95 ± 0.47 | 0.99 ± 0.04 | 1.00 ± 0.02 | 0.99 ± 0.04 | 0.89 ± 0.72 |
| L parotid | 0.99 ± 0.03 | 1.00 ± 0.01 | 1.00 ± 0.03 | 0.69 ± 0.43 | 0.97 ± 0.03 | 1.00 ± 0.01 | 0.97 ± 0.03 | 0.48 ± 0.36 |
| R Submandibular | 1.00 ± 0.04 | 1.00 ± 0.01 | 1.00 ± 0.05 | 1.21 ± 0.75 | 1.04 ± 0.02 | 1.02 ± 0.02 | 1.05 ± 0.02 | 1.74 ± 0.15 |
| shoulder | 0.95 ± 0.04 | 1.06 ± 0.02 | 0.96 ± 0.04 | 1.99 ± 0.03 | 0.96 ± 0.04 | 1.04 ± 0.04 | 0.97 ± 0.04 | 1.73 ± 0.09 |
| Mandible | 1.01 ± 0.00 | 1.01 ± 0.00 | 1.01 ± 0.00 | 1.06 ± 0.00 | 1.00 ± 0.00 | 1.00 ± 0.00 | 1.00 ± 0.00 | 0.98 ± 0.00 |

TABLE 7

| | 6 MV | | | | 10 MV | | | |
|---|---|---|---|---|---|---|---|---|
| Organs' name | Mean dose ratio | Max dose ratio | Mean BED ratio | NTCP ratio | Mean dose ratio | Max dose ratio | Mean BED ratio | NTCP ratio |
| VMAT | | | | | | | | |
| Cord | 0.98 ± 0.01 | 0.99 ± 0.01 | 0.98 ± 0.02 | 0.85 ± 0.03 | 0.99 ± 0.01 | 1.02 ± 0.01 | 1.00 ± 0.02 | 1.52 ± 0.53 |
| Esophagus | 0.99 ± 0.01 | 1.00 ± 0.01 | 0.99 ± 0.01 | 0.92 ± 0.19 | 1.01 ± 0.02 | 1.02 ± 0.03 | 1.01 ± 0.03 | 1.60 ± 0.84 |
| Heart | 0.94 ± 0.08 | 1.00 ± 0.01 | 0.94 ± 0.08 | 0.77 ± 0.28 | 0.94 ± 0.08 | 1.03 ± 0.02 | 0.94 ± 0.08 | 1.12 ± 0.50 |
| Larynx | 0.93 ± 0.04 | 0.98 ± 0.02 | 0.92 ± 0.04 | 0.60 ± 0.40 | 0.95 ± 0.03 | 0.99 ± 0.03 | 0.95 ± 0.04 | 0.95 ± 0.79 |
| Thyroid | 0.98 ± 0.00 | 1.00 ± 0.00 | 0.97 ± 0.00 | 0.97 ± 0.00 | 1.04 ± 0.00 | 1.06 ± 0.00 | 1.05 ± 0.00 | 1.09 ± 0.00 |
| BODY | 0.99 ± 0.01 | 1.01 ± 0.01 | 0.99 ± 0.01 | 1.03 ± 0.13 | 1.00 ± 0.01 | 1.03 ± 0.02 | 1.00 ± 0.01 | 1.41 ± 0.49 |
| Lungs | 0.99 ± 0.01 | 1.01 ± 0.01 | 0.99 ± 0.01 | 0.96 ± 0.09 | 0.99 ± 0.01 | 1.02 ± 0.01 | 0.99 ± 0.01 | 0.95 ± 0.06 |
| Carina | 1.00 ± 0.01 | 1.01 ± 0.01 | 1.00 ± 0.01 | 1.10 ± 0.15 | 1.01 ± 0.01 | 1.02 ± 0.01 | 1.02 ± 0.01 | 1.13 ± 0.19 |
| IMRT | | | | | | | | |
| Cord | 0.99 ± 0.01 | 1.00 ± 0.01 | 0.99 ± 0.02 | 0.96 ± 0.12 | 1.00 ± 0.03 | 1.01 ± 0.03 | 1.00 ± 0.03 | 1.25 ± 0.43 |
| Esophagus | 0.99 ± 0.00 | 1.01 ± 0.01 | 0.99 ± 0.00 | 1.09 ± 0.10 | 1.00 ± 0.01 | 1.00 ± 0.01 | 1.00 ± 0.01 | 1.02 ± 0.07 |
| Heart | 0.96 ± 0.06 | 1.00 ± 0.01 | 0.96 ± 0.06 | 0.96 ± 0.16 | 0.97 ± 0.06 | 0.99 ± 0.02 | 0.97 ± 0.07 | 1.12 ± 0.40 |
| Larynx | 0.97 ± 0.06 | 1.00 ± 0.01 | 0.97 ± 0.07 | 0.91 ± 0.47 | 0.99 ± 0.03 | 1.02 ± 0.03 | 0.99 ± 0.03 | 1.17 ± 0.18 |
| Thyroid | 1.00 ± 0.00 | 1.02 ± 0.00 | 1.00 ± 0.00 | 1.00 ± 0.00 | 1.02 ± 0.00 | 0.99 ± 0.00 | 1.02 ± 0.00 | 1.01 ± 0.00 |
| BODY | 1.00 ± 0.01 | 1.01 ± 0.02 | 1.00 ± 0.01 | 1.01 ± 0.01 | 1.00 ± 0.02 | 1.01 ± 0.01 | 1.00 ± 0.02 | 1.06 ± 0.06 |
| Lungs | 0.99 ± 0.00 | 1.00 ± 0.02 | 0.99 ± 0.00 | 0.93 ± 0.02 | 1.00 ± 0.01 | 0.99 ± 0.01 | 0.99 ± 0.00 | 0.96 ± 0.03 |
| Carina | 0.99 ± 0.00 | 1.00 ± 0.01 | 0.99 ± 0.00 | 0.96 ± 0.01 | 1.00 ± 0.01 | 1.00 ± 0.01 | 1.00 ± 0.01 | 1.04 ± 0.06 |

TABLE 8

| Organs' name | 6 MV | | | | 10 MV | | | |
|---|---|---|---|---|---|---|---|---|
| | Mean dose ratio | Max dose ratio | Mean BED ratio | NTCP ratio | Mean dose ratio | Max dose ratio | Mean BED ratio | NTCP ratio |
| VMAT | | | | | | | | |
| BODY | 0.98 ± 0.04 | 1.00 ± 0.00 | 0.98 ± 0.04 | 0.97 ± 0.07 | 0.99 ± 0.01 | 1.00 ± 0.04 | 0.99 ± 0.00 | 0.99 ± 0.04 |
| Rectum | 0.99 ± 0.01 | 1.00 ± 0.00 | 0.99 ± 0.01 | 1.01 ± 0.07 | 1.00 ± 0.02 | 1.01 ± 0.01 | 1.00 ± 0.02 | 1.05 ± 0.11 |
| Bladder | 0.99 ± 0.02 | 1.00 ± 0.01 | 0.99 ± 0.02 | 1.00 ± 0.15 | 1.00 ± 0.03 | 1.01 ± 0.01 | 1.00 ± 0.03 | 1.14 ± 0.44 |
| Rt hip | 0.95 ± 0.04 | 0.97 ± 0.04 | 0.95 ± 0.04 | 0.49 ± 0.33 | 0.95 ± 0.04 | 0.95 ± 0.05 | 0.95 ± 0.05 | 0.50 ± 0.43 |
| Lt hip | 0.98 ± 0.03 | 1.01 ± 0.01 | 0.97 ± 0.03 | 0.76 ± 0.28 | 0.95 ± 0.06 | 0.99 ± 0.04 | 0.94 ± 0.07 | 0.75 ± 0.57 |
| Penile bulb | 0.87 ± 0.09 | 0.93 ± 0.03 | 0.87 ± 0.09 | 0.23 ± 0.18 | 0.90 ± 0.03 | 0.93 ± 0.05 | 0.89 ± 0.03 | 0.33 ± 0.37 |
| IMRT | | | | | | | | |
| BODY | 1.01 ± 0.02 | 1.00 ± 0.01 | 1.01 ± 0.02 | 1.03 ± 0.07 | 1.01 ± 0.00 | 1.00 ± 0.01 | 1.01 ± 0.00 | 0.99 ± 0.08 |
| Rectum | 0.99 ± 0.01 | 1.00 ± 0.00 | 0.99 ± 0.01 | 0.98 ± 0.03 | 1.00 ± 0.00 | 1.00 ± 0.00 | 1.00 ± 0.00 | 0.99 ± 0.04 |
| Bladder | 1.00 ± 0.01 | 1.00 ± 0.01 | 1.00 ± 0.02 | 1.07 ± 0.26 | 1.01 ± 0.01 | 1.00 ± 0.00 | 1.01 ± 0.01 | 1.15 ± 0.21 |
| Rt hip | 1.00 ± 0.02 | 1.02 ± 0.01 | 0.99 ± 0.03 | 1.00 ± 0.44 | 1.00 ± 0.01 | 0.99 ± 0.00 | 1.00 ± 0.01 | 1.00 ± 0.18 |
| Lt hip | 1.00 ± 0.01 | 1.00 ± 0.02 | 1.00 ± 0.02 | 1.07 ± 0.23 | 1.01 ± 0.02 | 1.01 ± 0.01 | 1.01 ± 0.02 | 1.29 ± 0.35 |
| Penile bulb | 0.94 ± 0.03 | 0.95 ± 0.04 | 0.94 ± 0.03 | 0.50 ± 0.38 | 0.93 ± 0.04 | 0.94 ± 0.04 | 0.93 ± 0.04 | 0.41 ± 0.34 |

TABLE 9

IMRT

| Organs' name | 6 MV | | | | 10 MV | | | |
|---|---|---|---|---|---|---|---|---|
| | Mean dose ratio | Max dose ratio | Mean BED ratio | NTCP ratio | Mean dose ratio | Max dose ratio | Mean BED ratio | NTCP ratio |
| BREAST_CNTR | 0.95 | 0.91 | 0.95 | 0.65 | 1.01 | 0.88 | 1.01 | 0.78 |
| BREAST_IPSI | 1.00 | 1.02 | 1.00 | 1.00 | 1.01 | 1.03 | 1.01 | 1.02 |
| HEART | 0.94 | 1.01 | 0.94 | 0.73 | 0.97 | 1.02 | 0.97 | 0.96 |
| LUNG_CNTR | 0.94 | 0.93 | 0.94 | 0.59 | 1.01 | 0.95 | 1.01 | 1.02 |
| LUNG_IPSI | 0.99 | 1.00 | 0.99 | 0.92 | 1.01 | 1.01 | 1.01 | 1.07 |
| THYROID | 0.83 | 0.75 | 0.83 | 0.02 | 0.80 | 0.69 | 0.80 | 0.01 |
| BODY | 0.98 | 1.02 | 0.98 | 1.01 | 0.99 | 1.03 | 0.99 | 1.11 |

Among all four study-sites, some head and neck cancer targets required relatively larger field sizes (~16×20 cm²) to cover the PTV. With reference to FIGS. 9A, 9B, 10A and 10B, the FFF beam provides a lower mean dose to OARs in the VMAT plans. Dashed lines are the FFF beam plans and solid lines are the flattened beam plans. For the static IMRT plans, the FFF beam tends to provide higher doses to certain OARs.

In summary, the FFF beam provided comparative target coverage as compared with the flattened beam. In general, the FFF beam provided better dose sparing effect to OARs than the flattened beam. For clinical cases with relatively larger field sizes (~16×20 cm²), the FFF beam may lead to escalated dose to OARs in the static IMRT plans. Without intending to be bound to any particular theory, one possible explanation is that the large field size may allow for more soft photons in the beam. Thus, modifying the soft spectrum of the FFF beam may be necessary to provide improved treatment.

Figure 11:
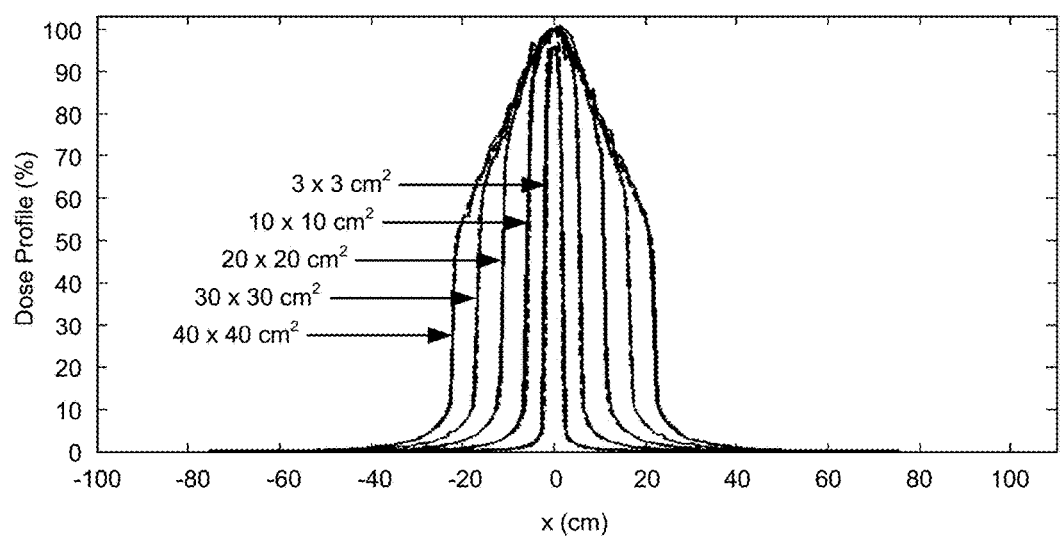
FIG. 11 is a plot that shows dose profiles of 6 MV FFF beam in the water tank at 10 cm depth with different field sizes and SSD=100 cm.

Detailed knowledge of the geometry and materials used in the gantry head may be useful for MC simulation. In order to precisely calculate the spectrum of photon beams, Varian provided the IAEA phase space files above the jaws (z=26.7 cm). To consider the geometry of the jaws, the VirtuaLinac web interface built on Amazon Web Services (AWS) system was used to calculate the new phase space data outside the gantry head (z=58 cm) for the TrueBeam system. Using the new generated phase space files as virtual source, BEAMnrc software based on the Electron-Gamma-Shower (EGSnrc) code was used to build the system. The energy of the beam was chosen to be 6 MV. It should be noted that all field sizes in the MC simulation were defined at 100 cm source-to-surface-distance (SSD). The cutoff energy for electron and photon were set to be 0.4 MeV and 0.01 MeV respectively. The SSD of the water tank was 100 cm. The calculation results were benchmarked with measured dose profiles at 10 cm depth in water (FIG. 11). All MC dose profiles were normalized by the dose value in the central axis. Close agreement was obtained between the MC simulation and the measured data for the TrueBeam system.

With respect to the Design of a SPECTER to modify the spectrum of the FFF beam, lead and tin were selected due to the general availability of these materials in clinics. Each layer of the SPECTER used a different size opening to avoid the central region in order to provide a high dose rate. Cross-sections were chosen to be circular and square. SPECTERs were attached to the gantry head in order to provide enough attenuation for the soft photons.

Figure 12B:
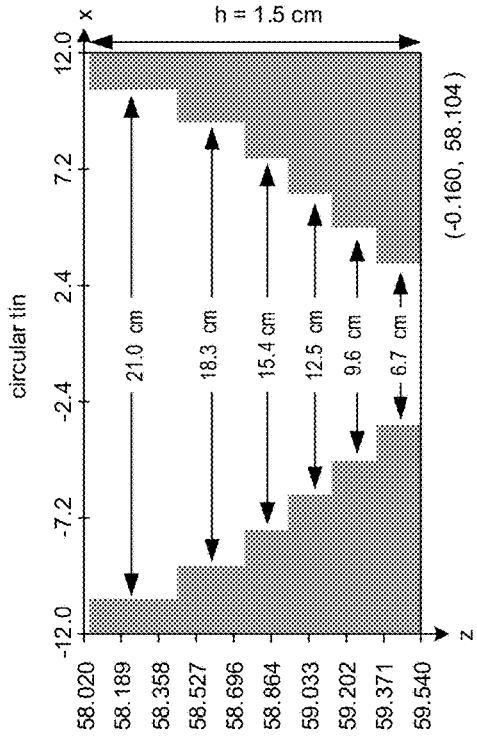
FIGS. 12A-12D show cross-sections of four different designs of the SPECTERs generated by previewRZ in the BEAMnrc software.
Figure 12D:
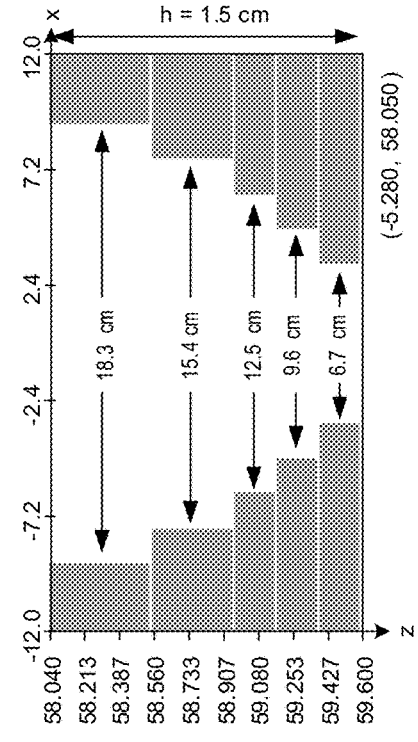
Figure 12A:
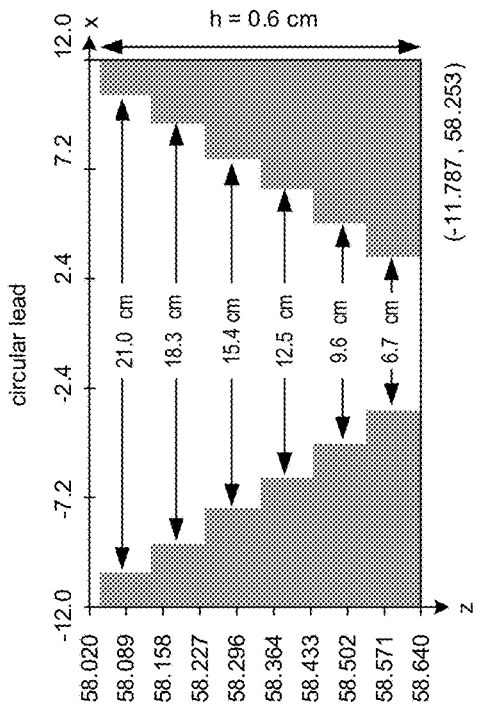
Figure 12C:
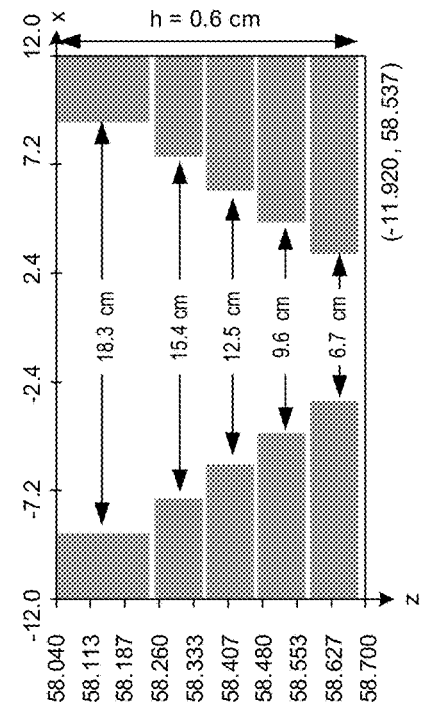

Four different designs of SPECTERs are shown in FIG. 12A-12D. Cross-sections of the central openings and peripheral materials were circular (FIGS. 12A and 12B) and square (FIGS. 12C and 12D). The total thicknesses were 0.6 cm for lead SPECTER (FIGS. 12A and 12C) and 1.5 cm for tin SPECTER (FIGS. 12 B and 12D). For FIGS. 12A and 12B, radiuses of the central opening were 10.5 cm, 9.15 cm. 7.7 cm, 6.25 cm, 4.8 cm and 3.35 cm from top to bottom. For FIGS. 12C and 12D, half of the side length of the central openings were 9.15 cm, 7.7 cm, 6.25 cm, 4.8 cm and 3.35 cm from top to bottom. For FIG. 12A, the thickness of each layer was 0.1 cm and the total thickness was 0.6 cm. For FIG. 12B, the thicknesses of the first two layers were 0.4 cm and 0.3 cm respectively and 0.2 cm for the rest layers from top to bottom. For FIG. 12C, the thicknesses were 0.2 cm for the first layer and 0.1 cm for the rest layers from top to the bottom. For FIG. 12D, thicknesses were 0.5 cm and 0.4 cm for the first two layers and 0.2 cm for the rest layers from top to bottom.

The present invention has been described in terms of one or more preferred embodiments, and it should be appreciated that many equivalents, alternatives, variations, and modifications, aside from those expressly stated, are possible and within the scope of the invention. Each reference identified in the present application is herein incorporated by reference in its entirety.

While present inventive concepts have been described with reference to particular embodiments, those of ordinary skill in the art will appreciate that various substitutions and/or other alterations may be made to the embodiments without departing from the spirit of present inventive concepts. Accordingly, the foregoing description is meant to be exemplary, and does not limit the scope of present inventive concepts.

A number of examples have been described herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

What is claimed is:

1. A radiation therapy system comprising:
an ionizing radiation source for producing a beam oriented along an axis aligned with a target volume for delivering ionizing radiation to the target volume along a beam path and at a dose rate, wherein the beam includes a soft spectrum and a hard spectrum;
a filter arranged within the beam path and including a central aperture that is free of beam-filtering material, wherein the central aperture is surrounded by a beam filtering material having a thickness dimension selected and positioned in the beam path to highly attenuate the soft spectrum of the beam to reduce external scatter of the beam and allow a majority of the hard spectrum of the beam to pass through the central aperture unfiltered;
wherein the filter includes a concave profile surrounding the central aperture; and
wherein the beam path is free of beam-filtering material arranged to attenuate a central portion of the beam.

2. The system of claim 1 wherein the central aperture is arranged along a central axis of the beam.

3. The system of claim 2 wherein the filter extends along the beam path from a base to a pinnacle located between the central aperture and a periphery.

4. The system of claim 3 wherein the periphery encloses the central aperture and is formed of beam-filtering material.

5. The system of claim 3 further comprising a taper extending between the central aperture and the pinnacle.

6. The system of claim 5 wherein a size of the central aperture and the taper is selected to highly attenuate the soft spectrum of the beam to reduces external scatter of the beam and allow a majority of the hard spectrum of the beam to pass through the central aperture unfiltered.

7. The system of claim 5 wherein the taper is discontinuously formed of steps.

8. The system of claim 5 wherein the taper is formed of a continuous slope.

9. The system of claim 5 further comprising a second taper extending between the pinnacle and the periphery.

10. The system of claim 3 wherein the periphery forms a circular shape or a square shape.

11. The system of claim 1 wherein the central aperture forms a circular shape or a square shape.

12. The system of claim 1 wherein the beam has a cone shape or a fan shape.

13. The system of claim 1 further comprising a collimator arranged in the beam path.

14. The system of claim 13 wherein the filter is arranged between the ionizing radiation source and the collimator.

15. The system of claim 1 wherein the beam-filtering material includes tin or lead.

16. The system of claim 1 further comprising a gantry forming a housing about the ionizing radiation source and wherein the filter is housed in the gantry.

17. The system of claim 1 wherein the ionizing radiation source includes a linear accelerator.

18. The system of claim 1 wherein the radiation therapy system forms an intensity modulated radiation therapy (IMRT) system.

19. The system of claim 1 wherein the radiation therapy system forms an image guided radiation therapy system.

20. A radiation therapy system comprising:
an ionizing radiation source for producing a beam oriented along an axis aligned with a target volume for delivering ionizing radiation to the target volume along a beam path and at a dose rate, wherein the beam includes a soft spectrum and a hard spectrum;
a filter arranged within the beam path and including a central aperture that is free of beam-filtering material, wherein the central aperture is surrounded by a beam filtering material having a thickness dimension selected and positioned in the beam path to highly attenuate the soft spectrum of the beam to reduce external scatter of the beam and allow a majority of the hard spectrum of the beam to pass through the central aperture unfiltered;
wherein the thickness dimension of the beam-filtering material increases from an inner thickness at the central aperture to a maximum thickness at a pinnacle and then decreases to an outer thickness at a periphery of the filter; and
wherein the beam path is free of beam-filtering material arranged to attenuate a central portion of the beam.

21. The system of claim 20 further comprising a taper extending between the central aperture and the pinnacle.

22. The system of claim 21 further comprising a second taper extending between the pinnacle and the periphery.

* * * * *